(12) United States Patent
Ohishi et al.

(10) Patent No.: US 9,036,777 B2
(45) Date of Patent: May 19, 2015

(54) MEDICAL IMAGE PROCESSING APPARATUS

(75) Inventors: Satoru Ohishi, Otawara (JP); Hisato Takemoto, Nasushiobara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 274 days.

(21) Appl. No.: 13/618,958

(22) Filed: Sep. 14, 2012

(65) Prior Publication Data

US 2013/0010924 A1    Jan. 10, 2013

Related U.S. Application Data

(63) Continuation of application No. PCT/JP2012/064405, filed on Jun. 4, 2012.

(30) Foreign Application Priority Data

Jun. 6, 2011    (JP) .................................. 2011-126657

(51) Int. Cl.
   *A61B 6/02*    (2006.01)
   *A61B 6/12*    (2006.01)
   *A61B 6/00*    (2006.01)

(52) U.S. Cl.
   CPC . *A61B 6/022* (2013.01); *A61B 6/12* (2013.01); *A61B 6/4014* (2013.01);
   (Continued)

(58) Field of Classification Search
   CPC ........ A61B 6/022; A61B 6/12; A61B 6/4014; A61B 6/4028; A61B 6/466; A61B 6/481; A61B 6/487; A61B 6/5205
   USPC .................................... 378/41, 42, 65, 98.12
   See application file for complete search history.

(56) References Cited

U.S. PATENT DOCUMENTS 5,852,646 A  *  12/1998  Klotz et al. ........................ 378/8
5,901,199 A  *   5/1999  Murphy et al. .................. 378/65
(Continued)

FOREIGN PATENT DOCUMENTS

CN    101238351 A    8/2008
CN    101803930 A    8/2010
(Continued)

OTHER PUBLICATIONS

Combined Office Action and Search Report issued Jun. 4, 2014, in Chinese Patent Application No. 201280001606.6 with English translation of category of cited documents.
(Continued)

*Primary Examiner* — Allen C. Ho
(74) *Attorney, Agent, or Firm* — Oblon, McClelland, Maier & Neustadt, L.L.P.

(57) ABSTRACT

A medical image processing apparatus according to an embodiment includes: an imaging unit configured to image an affected area in two directions using X-rays; a fluoroscopic image generating unit configured to generate two X-ray fluoroscopic images corresponding to the two directions, on a basis of imaging signals outputted from the imaging unit; a rendering image generating unit configured to project the affected area contained in three-dimensional image data acquired in advance, in two directions according to a same X-ray geometry as that used for imaging the X-ray fluoroscopic images, to thereby generate two affected area rendering images; and an image combining unit configured to combine the X-ray fluoroscopic images with the affected area rendering images for each corresponding direction, to thereby generate combined parallax images in two parallax directions corresponding to the two directions, and to output the two generated combined parallax images to a 3D display apparatus.

6 Claims, 20 Drawing Sheets

(52) U.S. Cl.
CPC ............. *A61B 6/4028* (2013.01); *A61B 6/466* (2013.01); *A61B 6/481* (2013.01); *A61B 6/487* (2013.01); *A61B 6/5205* (2013.01)

(56) References Cited

U.S. PATENT DOCUMENTS

| | | | | |
|---|---|---|---|---|
| 6,118,848 | A * | 9/2000 | Reiffel | 378/65 |
| 6,125,164 | A * | 9/2000 | Murphy et al. | 378/65 |
| 6,307,914 | B1 * | 10/2001 | Kunieda et al. | 378/65 |
| 6,449,333 | B1 * | 9/2002 | Yamasaki | 378/42 |
| 6,516,046 | B1 * | 2/2003 | Frohlich et al. | 378/65 |
| 6,711,433 | B1 * | 3/2004 | Geiger et al. | 600/431 |
| 6,865,253 | B2 * | 3/2005 | Blumhofer et al. | 378/65 |
| 6,980,626 | B2 * | 12/2005 | Groh et al. | 378/87 |
| 7,035,371 | B2 * | 4/2006 | Boese et al. | 378/41 |
| 7,079,620 | B2 * | 7/2006 | Vaillant et al. | 378/41 |
| 7,145,980 | B2 * | 12/2006 | Sakaguchi et al. | 378/7 |
| 7,204,640 | B2 * | 4/2007 | Fu et al. | 378/205 |
| 7,209,538 | B2 * | 4/2007 | Sukovic et al. | 378/42 |
| 7,227,925 | B1 * | 6/2007 | Mansfield et al. | 378/65 |
| 7,260,179 | B2 * | 8/2007 | Gunzler et al. | 378/98.4 |
| 7,302,033 | B2 * | 11/2007 | Carrano et al. | 378/65 |
| 7,436,928 | B2 * | 10/2008 | Urano et al. | 378/65 |
| 7,453,983 | B2 * | 11/2008 | Schildkraut et al. | 378/65 |
| 7,453,984 | B2 * | 11/2008 | Chen et al. | 378/65 |
| 7,502,443 | B1 * | 3/2009 | Haynes et al. | 378/65 |
| 7,558,372 | B2 * | 7/2009 | Zellerhoff | 378/98.12 |
| 7,620,144 | B2 * | 11/2009 | Bodduluri | 378/41 |
| 7,623,623 | B2 * | 11/2009 | Raanes et al. | 378/65 |
| 7,656,998 | B2 * | 2/2010 | Main et al. | 378/65 |
| 7,660,381 | B2 * | 2/2010 | Joosten et al. | 378/7 |
| 7,689,042 | B2 * | 3/2010 | Brunner et al. | 382/199 |
| 7,693,256 | B2 * | 4/2010 | Brahme et al. | 378/41 |
| 7,835,500 | B2 * | 11/2010 | Fu et al. | 378/128 |
| 7,852,984 | B2 * | 12/2010 | Zellerhoff | 378/98.12 |
| 7,894,649 | B2 * | 2/2011 | Fu et al. | 382/128 |
| 7,933,378 | B2 * | 4/2011 | Proksa | 378/9 |
| 7,949,089 | B2 * | 5/2011 | Dafni et al. | 378/9 |
| 8,086,004 | B2 * | 12/2011 | Kuduvalli et al. | 382/128 |
| 8,090,175 | B2 * | 1/2012 | Fu et al. | 382/128 |
| 8,126,236 | B2 * | 2/2012 | Harer et al. | 382/130 |
| 8,180,017 | B2 * | 5/2012 | Forthmann et al. | 378/9 |
| 8,417,318 | B2 * | 4/2013 | West | 600/424 |
| 8,457,372 | B2 * | 6/2013 | Fu et al. | 382/128 |
| 8,538,505 | B2 * | 9/2013 | Brunner et al. | 600/428 |
| 8,559,596 | B2 * | 10/2013 | Thomson et al. | 378/65 |
| 2005/0207529 | A1 | 9/2005 | Boese et al. | |
| 2007/0003007 | A1 | 1/2007 | Carrano et al. | |
| 2010/0208973 | A1 * | 8/2010 | Lienard et al. | 382/132 |

FOREIGN PATENT DOCUMENTS

| | | |
|---|---|---|
| JP | 03-123537 | 5/1991 |
| JP | 10-057365 | 3/1998 |
| JP | 2000-102529 | 4/2000 |
| JP | 2005-270652 | 10/2005 |
| JP | 2011-036474 | 2/2011 |

OTHER PUBLICATIONS

International Preliminary Report on Patentability and Written Opinion issued Dec. 10, 2013 in PCT/JP2012/064405 (submitting English translation only).

Combined Chinese Office Action and Search Report issued Dec. 5, 2014 in Patent Application No. 201280001606.6 (with English Translation of Categories of Cited Documents).

* cited by examiner

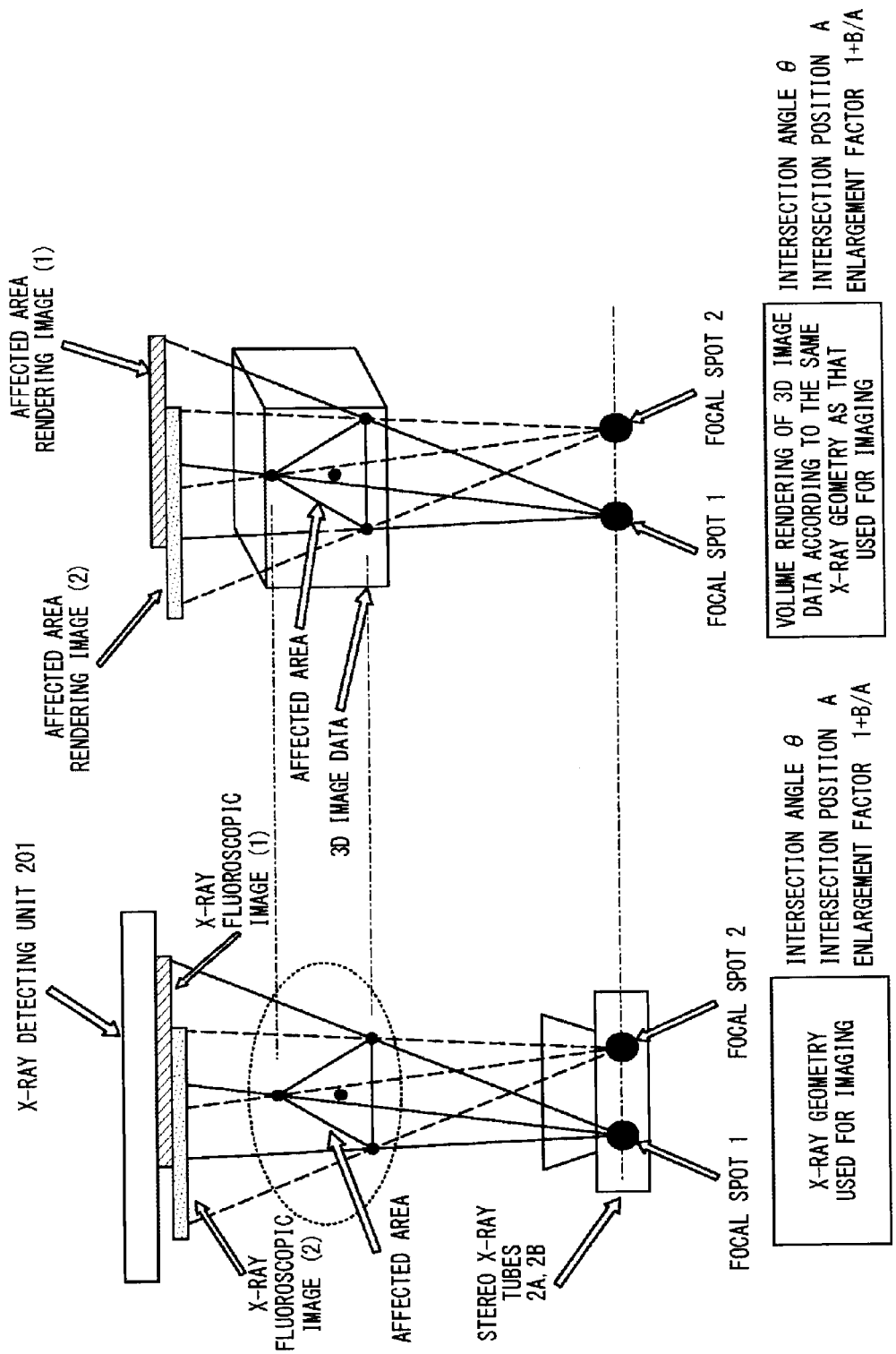

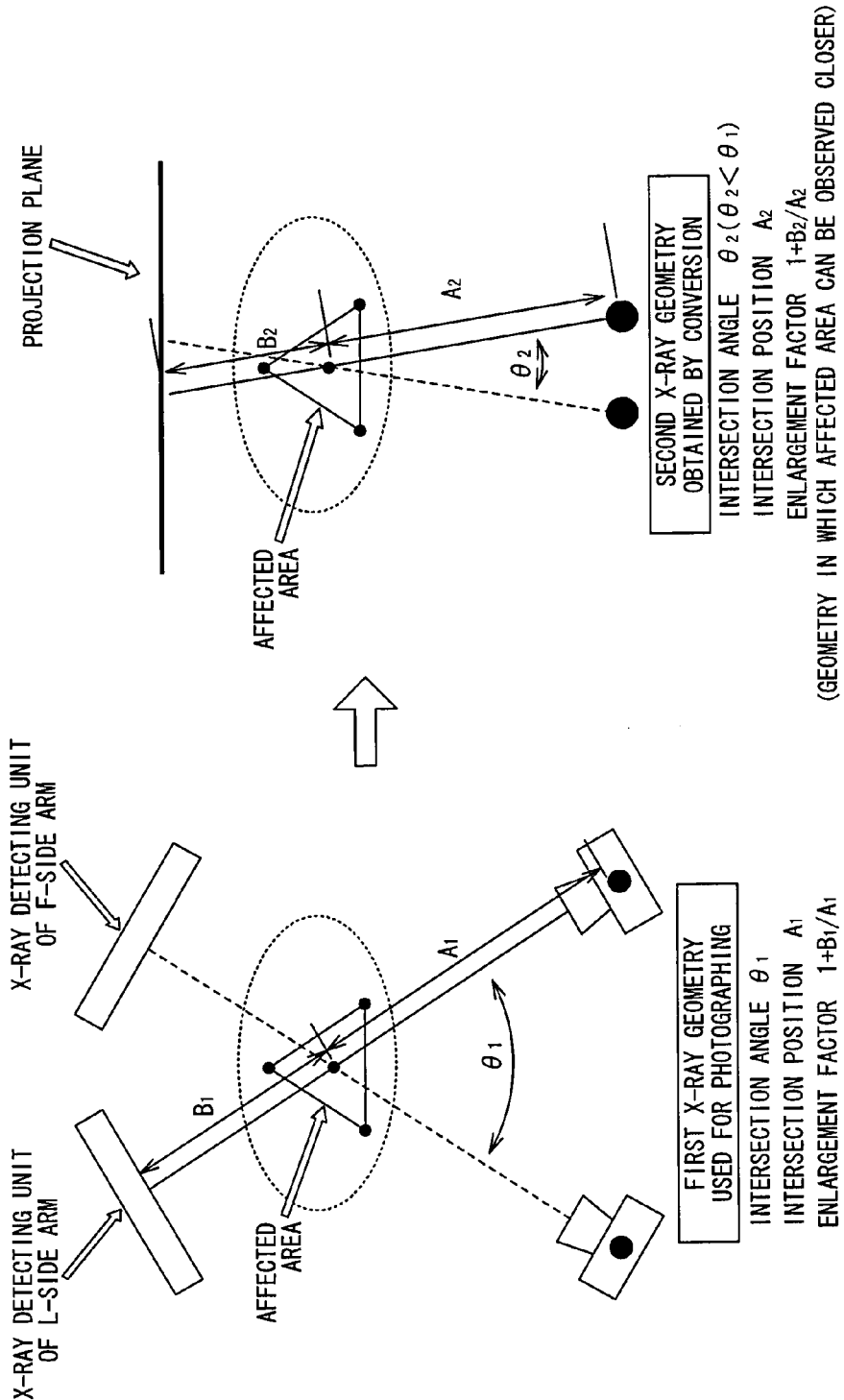

MEDICAL IMAGE PROCESSING APPARATUS

CROSS-REFERENCE TO RELATED APPLICATIONS

This application is a Continuation Application of No. PCT/JP2012/064405, filed Jun. 4, 2012, and the PCT application is based upon and claims the benefit of priority from Japanese Patent Applications No. 2011-126657 filed on Jun. 6, 2011, the entire contents of which are incorporated herein by reference.

FIELD

Embodiments of the present invention relate to a medical image processing apparatus.

BACKGROUND

A coiling treatment for an aneurysm is exemplified as one of catheter treatments. In the coiling treatment, a leading end of a catheter is inserted into the aneurysm, a thin soft coil is taken out of the leading end of the catheter, and an inside of the aneurysm is filled with the coil. Where to place the leading end of the catheter inside of the aneurysm is extremely important in the coiling treatment. Accordingly, in general, during the treatment, a vicinity of the aneurysm is imaged using an X-ray imaging apparatus, and a real-time image on a display is monitored.

Examples of the X-ray imaging apparatus used in such a catheter treatment include a normal X-ray imaging apparatus of a single-plane type, and also include: an X-ray imaging apparatus of a biplane type that is capable of imaging in two directions at the same time; an X-ray imaging apparatus including stereo X-ray tubes having two X-ray focal spots; and an X-ray imaging apparatus that photographs an object while moving one X-ray tube around the object and generates an image that can be stereoscopically observed (Japanese Patent Laid-Open No. 03-123537 and the like).

The X-ray imaging apparatus having stereo X-ray tubes or the X-ray imaging apparatus that photographs an object while moving one X-ray tube around the object enable stereoscopic view of an affected area, so that the affected area can be stereoscopically observed.

Meanwhile, a large number of blood vessels run in a head region in a complicated and intricate manner. In addition, as described above, a setting position of a leading end of a catheter is extremely important in the coiling treatment and the like for an aneurysm in a head region, but conventional stereoscopic images cannot necessarily provide an operator with a satisfactory sense of depth and a satisfactory stereoscopic effect.

Under the circumstances, there is a demand for a medical image processing apparatus that enables an operator to easily understand a front-back and right-left positional relation of blood vessels in and around an affected area of an aneurysm or the like, and provides a stereoscopic image that contributes to an accurate catheter operation without any error, even in an area in which the blood vessels run in a complicated and intricate manner.

SUMMARY

A medical image processing apparatus according to an embodiment includes: an imaging unit configured to image an affected area in two directions using X-rays; a fluoroscopic image generating unit configured to generate two X-ray fluoroscopic images corresponding to the two directions, on a basis of imaging signals outputted from the imaging unit; a rendering image generating unit configured to project the affected area contained in three-dimensional image data acquired in advance, in two directions according to a same X-ray geometry as that used for imaging the X-ray fluoroscopic images, to thereby generate two affected area rendering images; and an image combining unit configured to combine the X-ray fluoroscopic images with the affected area rendering images for each corresponding direction, to thereby generate combined parallax images in two parallax directions corresponding to the two directions, and to output the two generated combined parallax images to a 3D display apparatus.

BRIEF DESCRIPTION OF DRAWINGS

FIGS. 5(A) and 5(B) are views for describing a relation between an X-ray geometry used for photographing and the same X-ray geometry used for rendering;

FIGS. 20(A) and 20(B) are views for describing a relation between a first X-ray geometry and a second X-ray geometry used for rendering according to the fifth embodiment.

DESCRIPTION OF EMBODIMENTS

Hereinafter, embodiments of the present invention are described with reference to the attached drawings.

(1) First Embodiment

Figure 1:
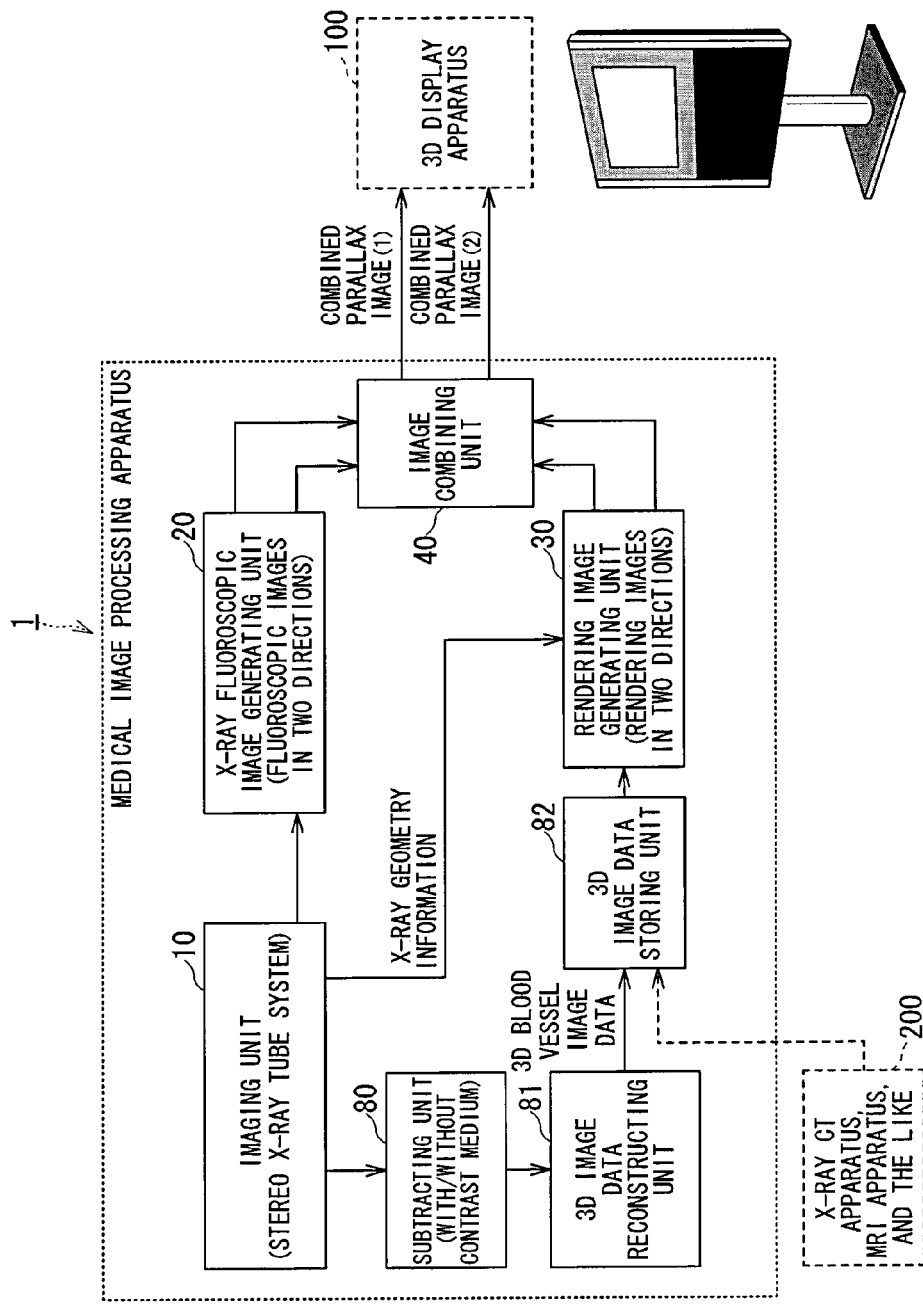
FIG. 1 is a block diagram illustrating a configuration example of a medical image processing apparatus according to a first embodiment.

FIG. 1 is a block diagram illustrating a configuration example of a medical image processing apparatus 1 according to a first embodiment. The medical image processing apparatus 1 includes an imaging unit 10, an X-ray fluoroscopic image generating unit 20, a rendering image generating unit 30, an image combining unit 40, a subtracting unit 80, a three-dimensional (3D) image data reconstructing unit 81, and a three-dimensional (3D) image data storing unit 82.

The imaging unit 10 according to the first embodiment is of a stereo X-ray tube system. The imaging unit 10 includes two first and second X-ray focal spots. The imaging unit 10 causes one X-ray detecting unit 201 to detect emitted X-rays while making switching between the first and second X-ray focal spots, and fluoroscopically images an affected area in two directions using X-rays.

The X-ray fluoroscopic image generating unit 20 generates two X-ray fluoroscopic images corresponding to the two directions, on the basis of imaging signals outputted from the imaging unit 10.

The rendering image generating unit 30 projects three-dimensional image data stored in the 3D image data storing unit 82, in two directions according to the same X-ray geometry as that used for photographing the X-ray fluoroscopic images by the imaging unit 10, and generates two volume rendering images. The three-dimensional image data is volume data containing an affected area of the same patient, and is acquired in advance before the X-ray fluoroscopic images are imaged. The volume rendering images contain image data of the affected area, and thus are referred to as "affected area rendering images" in some cases.

The image combining unit 40 respectively combines the X-ray fluoroscopic images with the volume rendering images for each corresponding direction to generate combined parallax images in two parallax directions corresponding to the two directions, and outputs the two combined parallax images to a 3D display apparatus 100.

The 3D display apparatus 100 may be a 3D display equipped with glasses, or may be a glasses-free 3D display that does not require special glasses. In the 3D display equipped with glasses, the two combined parallax images (1) and (2), that is, two images for left and right parallaxes outputted by the image combining unit 40 are separated by glasses with a polarizing filter or glasses with a liquid crystal shutter, whereby a sense of depth of a three-dimensional object is given to an observer.

On the other hand, in the glasses-free 3D display, multi-parallax images (for example, nine-parallax images) are generated from the two images for left and right parallaxes. Then, the multi-parallax images are distributed in a plurality of parallax directions (for example, nine-parallax directions) by a cylindrical lens called lenticular lens. As a result, a sense of depth of a three-dimensional object can be given to an observer without any special glasses. In addition, in the case of the glasses-free 3D display, when the observer moves around the display apparatus, such a stereoscopic effect as if the observer actually moved for observation around the three-dimensional object can be given to the observer.

Operations of the subtracting unit 80 and the 3D image data reconstructing unit 81 will be described later.

A detailed operation of the medical image processing apparatus 1 configured as described above is described with reference to a flow chart of FIG. 2.

Figure 3:
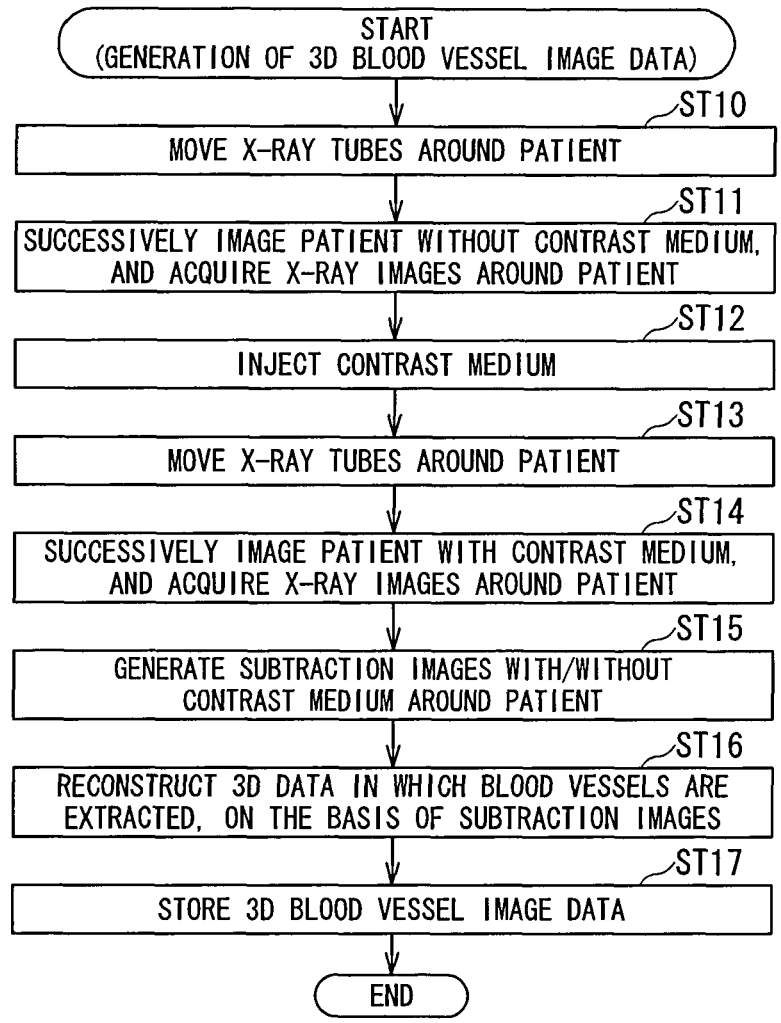
FIG. 3 is a flow chart illustrating a processing example of three-dimensional image data generation.

In Step ST1, three-dimensional blood vessel image data is generated, and is stored in the 3D image data storing unit 82. FIG. 3 is a flow chart illustrating a detailed operation of Step ST1.

In Step ST10 of FIG. 3, before a contrast medium is introduced into a patient, X-ray tubes are moved around the patient, and fluoroscopic images of the patient are successively photographed. Then, X-ray fluoroscopic images around the patient without the contrast medium are acquired (Step ST11).

Next, the contrast medium is introduced into the patient (Step ST12), the X-ray tubes are moved around the patient (Step ST13), and X-ray fluoroscopic images around the patient with the contrast medium are acquired this time (Step ST14). Next, the acquired X-ray fluoroscopic images without/with the contrast medium are subjected to subtraction and subtraction images around the patient are generated (Step ST15). Parenchymal portions other than blood vessels are canceled by the subtraction, and hence only the blood vessels are extracted on the subtraction images. Next, the generated subtraction images around the patient are reconstructed, and three-dimensional blood vessel image data in which only the blood vessels are extracted is reconstructed (Step ST16). An algorithm for the reconstruction is not particularly limited, and, for example, weighted filtered back-projection proposed by Feldkamp et al. is used therefor. Then, the reconstructed three-dimensional blood vessel image data is stored in the 3D image data storing unit 82 (Step ST17).

Note that the three-dimensional blood vessel image data may be acquired using the imaging unit 10 of this apparatus as described above, or alternatively may be acquired in advance using other modalities such as an X-ray CT apparatus and an MRI apparatus 200.

The processes in Steps ST11, ST14, and ST15 of the above-mentioned steps are performed by the subtracting unit 80. In addition, the process in Step ST16 is performed by the 3D image data reconstructing unit 81.

Returning to FIG. 2, in Step ST2, X-ray geometry information, which is used when an affected area is fluoroscopically imaged using the stereo X-ray tubes, is acquired from the imaging unit 10, and is given to the rendering image generating unit 30.

Figures 4A, 4B:
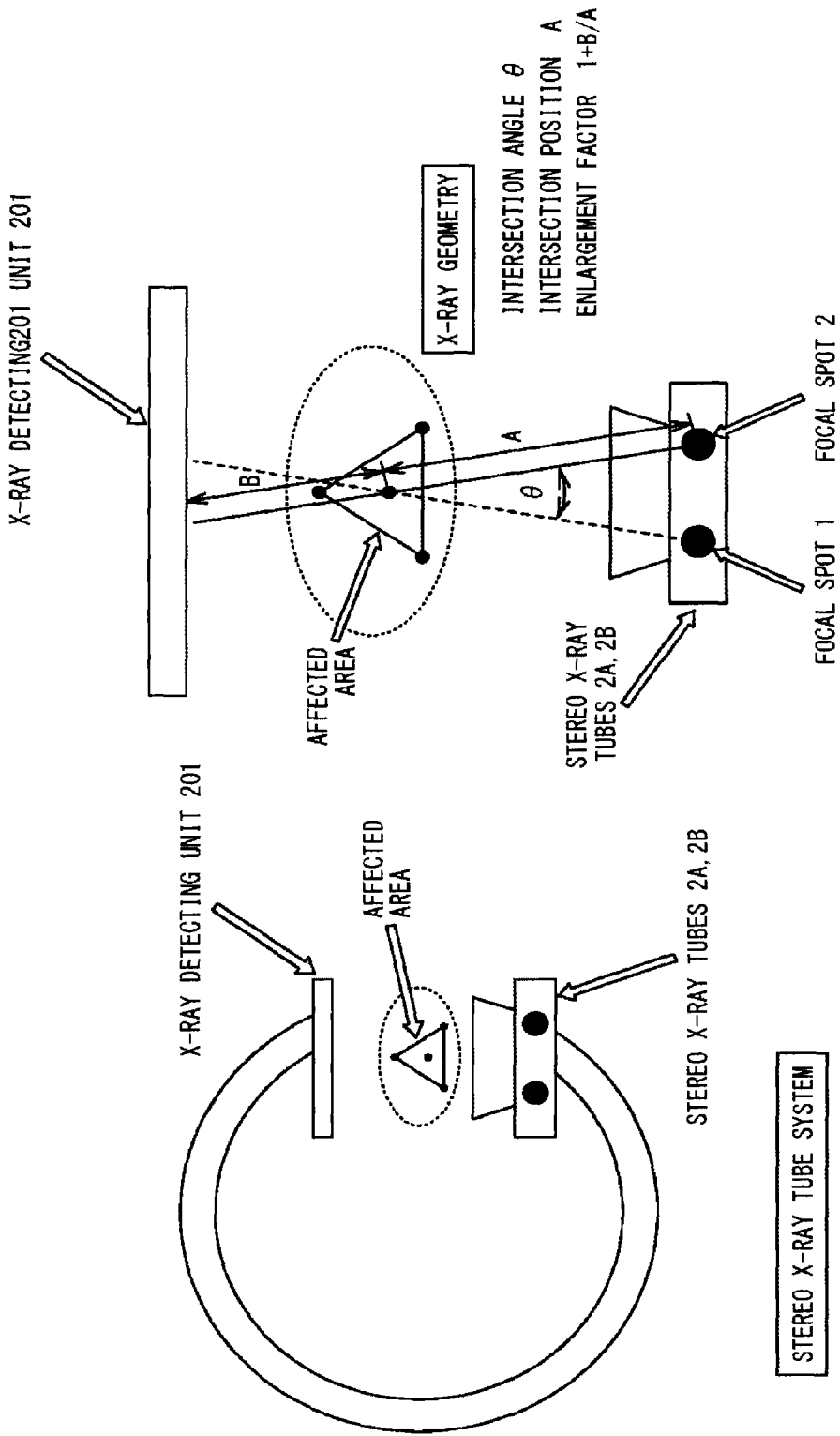
FIGS. 4(A) and 4(B) are views for describing an X-ray geometry of a stereo X-ray tube system.

FIGS. 4(A) and 4(B) are views for describing an X-ray geometry of the stereo X-ray tube system. The X-ray geometry refers to a geometric positional relation as illustrated in FIG. 4(B) that is determined, e.g., by an intersection angle θ, an intersection position "A", and an enlargement factor "1+B/A" in a situation in which two X-ray center trajectories intersect each other, and respectively pass through focal spots 1 and 2 of the two X-ray tubes 2A and 2B and the center (isocenter) of the affected area.

Figure 2:
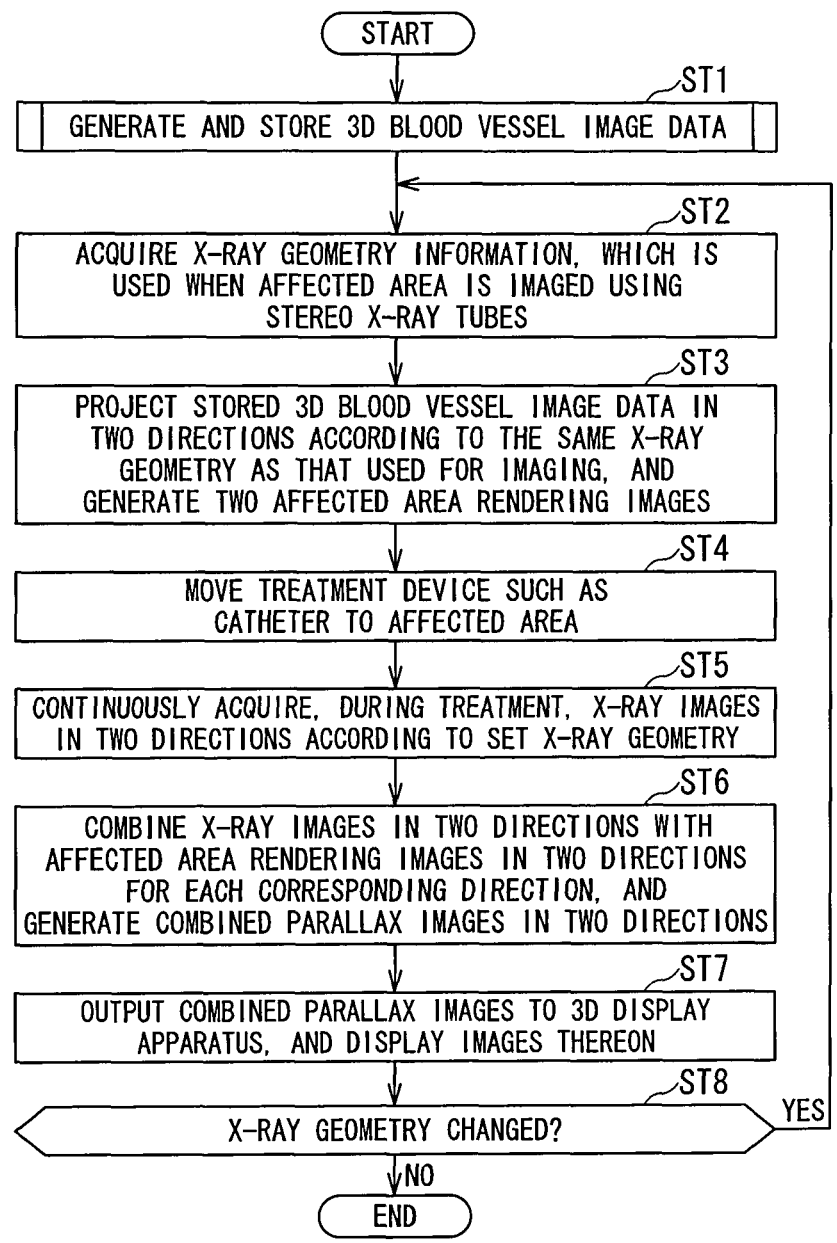
FIG. 2 is a flow chart illustrating an operation example of the medical image processing apparatus according to the first embodiment.
Figure 6:
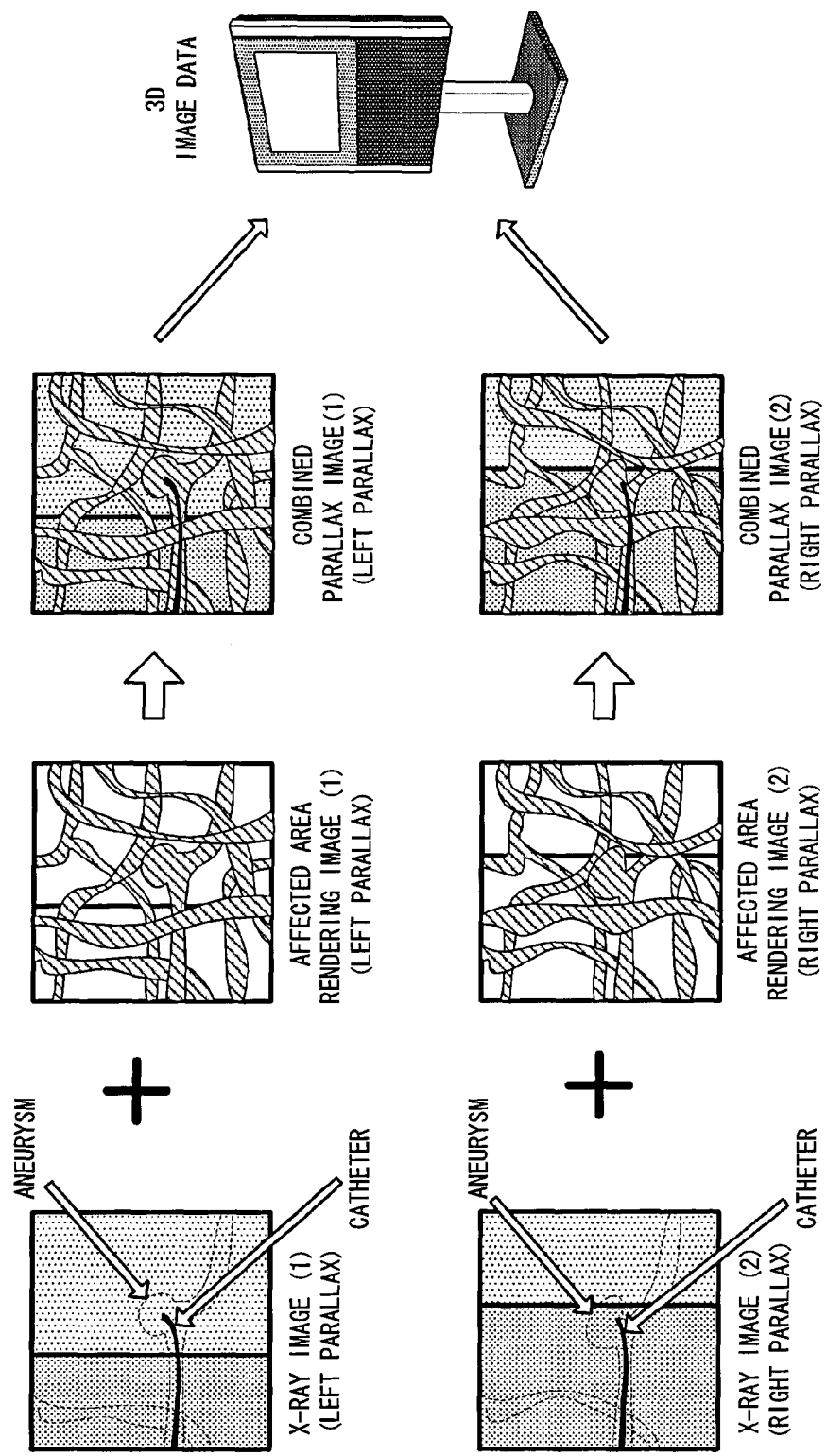
FIG. 6 is a view for describing a generation concept of combined parallax images according to the first embodiment.

In Step ST3 of FIG. 2, the stored three-dimensional blood vessel image data is projected in two directions according to the same X-ray geometry as that used for the fluoroscopic imaging, and two affected area rendering images (1) and (2)

are generated. FIG. 5(B) is a view schematically illustrating how the two affected area rendering images (1) and (2) are generated. The affected area rendering images (1) and (2) are generated by the rendering image generating unit 30. The generated affected area rendering images (1) and (2) are stored in an appropriate memory included in the rendering image generating unit 30. FIG. 6 illustrates, in its center, schematic images of the affected area rendering image (1) (for left parallax) and the affected area rendering image (2) (for right parallax) on which only blood vessels of a head region are extracted.

When a doctor starts to move a treatment device such as a catheter to an affected area, for example, an aneurysm in the head region (Step ST4), X-ray fluoroscopic images are continuously acquired and generated during the treatment in the two directions according to the set X-ray geometry (Step ST5). FIG. 5(A) is a view for describing a situation where the X-ray fluoroscopic images (1) and (2) are imaged in the two directions. FIG. 6 illustrates, in its left, schematic images of the X-ray fluoroscopic image (1) (for left parallax) and the X-ray fluoroscopic image (2) (for right parallax) when a leading end of the catheter is moved to a position of the aneurysm. At this time, since a contrast medium is not injected, blood vessels and an aneurysm are not imaged, while the catheter and the parenchymal portions are imaged. The X-ray fluoroscopic images are generated by the X-ray fluoroscopic image generating unit 20.

In Step ST6, as illustrated in FIG. 6 in its right, the two X-ray fluoroscopic images (1) and (2) in the two directions are combined for each corresponding direction with the two affected area rendering images (1) and (2) projected according to the same X-ray geometry, and combined parallax images (1) and (2) are generated in the two directions. The combined parallax images (1) and (2) are generated by the image combining unit 40.

The image combining unit 40 outputs the generated combined parallax images (1) and (2) in the two directions to the 3D display apparatus 100, and the combined images are three-dimensionally displayed on the 3D display apparatus 100 (Step ST7).

If the X-ray geometry is changed by an operation of a doctor or the like, the processing returns to Step ST2. If the X-ray geometry is not changed, the processing is ended (Step ST8).

In the medical image processing apparatus 1 according to the first embodiment, even in the case of a treatment for an aneurysm or the like in a head region in which blood vessels run in a complicated manner, images are displayed on the 3D display apparatus 100 such that X-ray fluoroscopic images, which taken in right and left parallax directions using the stereo X-ray tubes, are superimposed on rendering images, which are obtained by projecting three-dimensional blood vessel images of the head region according to the same X-ray geometry as that used for the X-ray fluoroscopic photographing. Accordingly, even in the case of a coiling treatment for an aneurysm or the like in a head region in which blood vessels run in a complicated manner, an operation of a catheter and the like can be easily and accurately performed.

Incidentally, when the catheter is moved to a position near the aneurysm, the blood vessel may be deformed by an extending force of the catheter, causing a position shift of the aneurysm. In order to observe the position shift of the aneurysm, it is preferable to obtain X-ray fluoroscopic images (1) and (2) including not only the catheter but also the aneurysm. For this purpose, a contrast medium may be injected from both sides when the catheter comes close to the aneurysm, resulting in fluoroscopic images (1) and (2) including the aneurysm shifted by the extending force of the catheter. In addition, the position of the aneurysm in each of the two affected area rendering images (1) and (2) may be corrected by comparing them with the position of the aneurysm in the obtained X-ray fluoroscopic images (1) and (2).

(2) Second Embodiment

Figure 7:
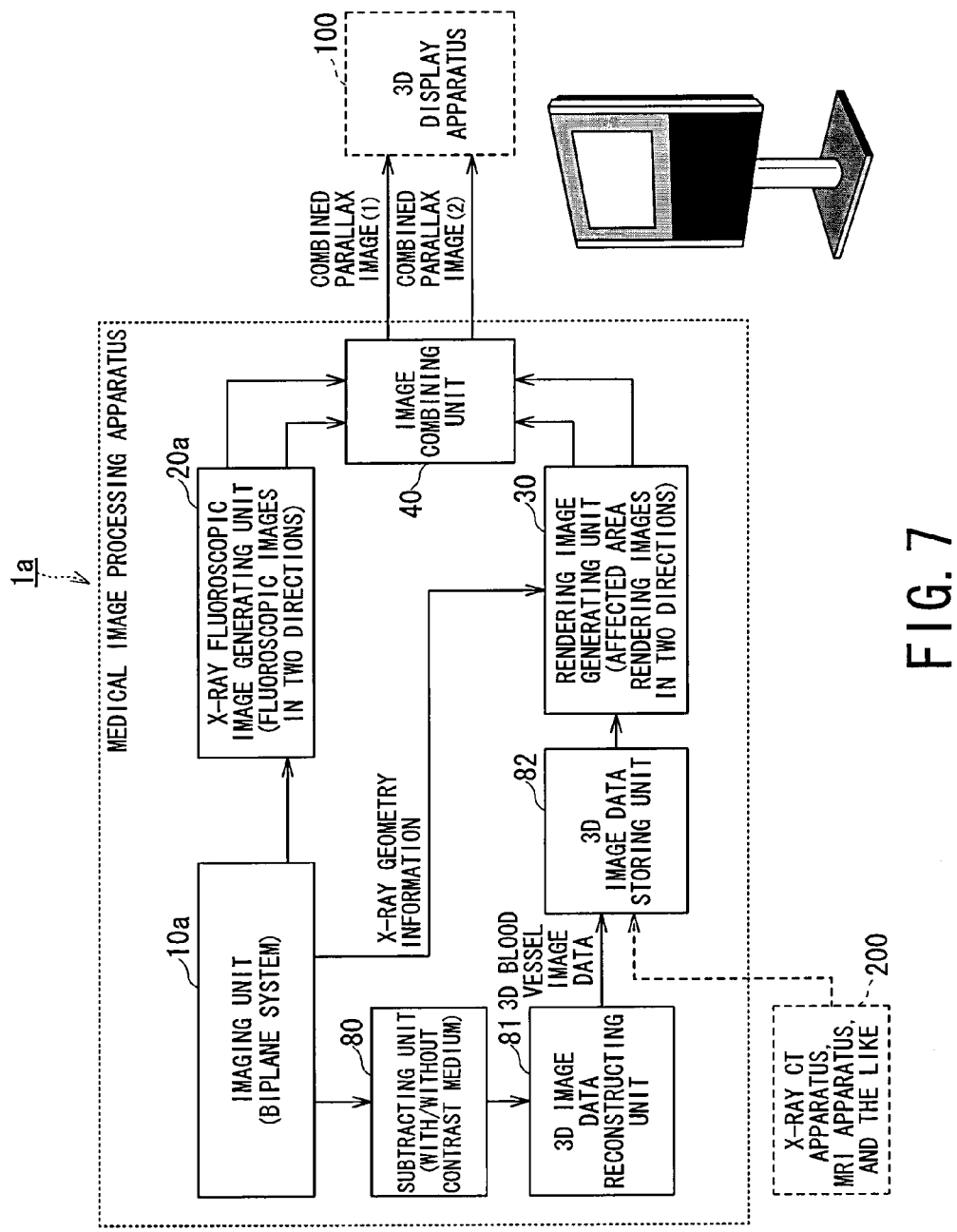
FIG. 7 is a block diagram illustrating a configuration example of a medical image processing apparatus according to a second embodiment.
Figure 9:
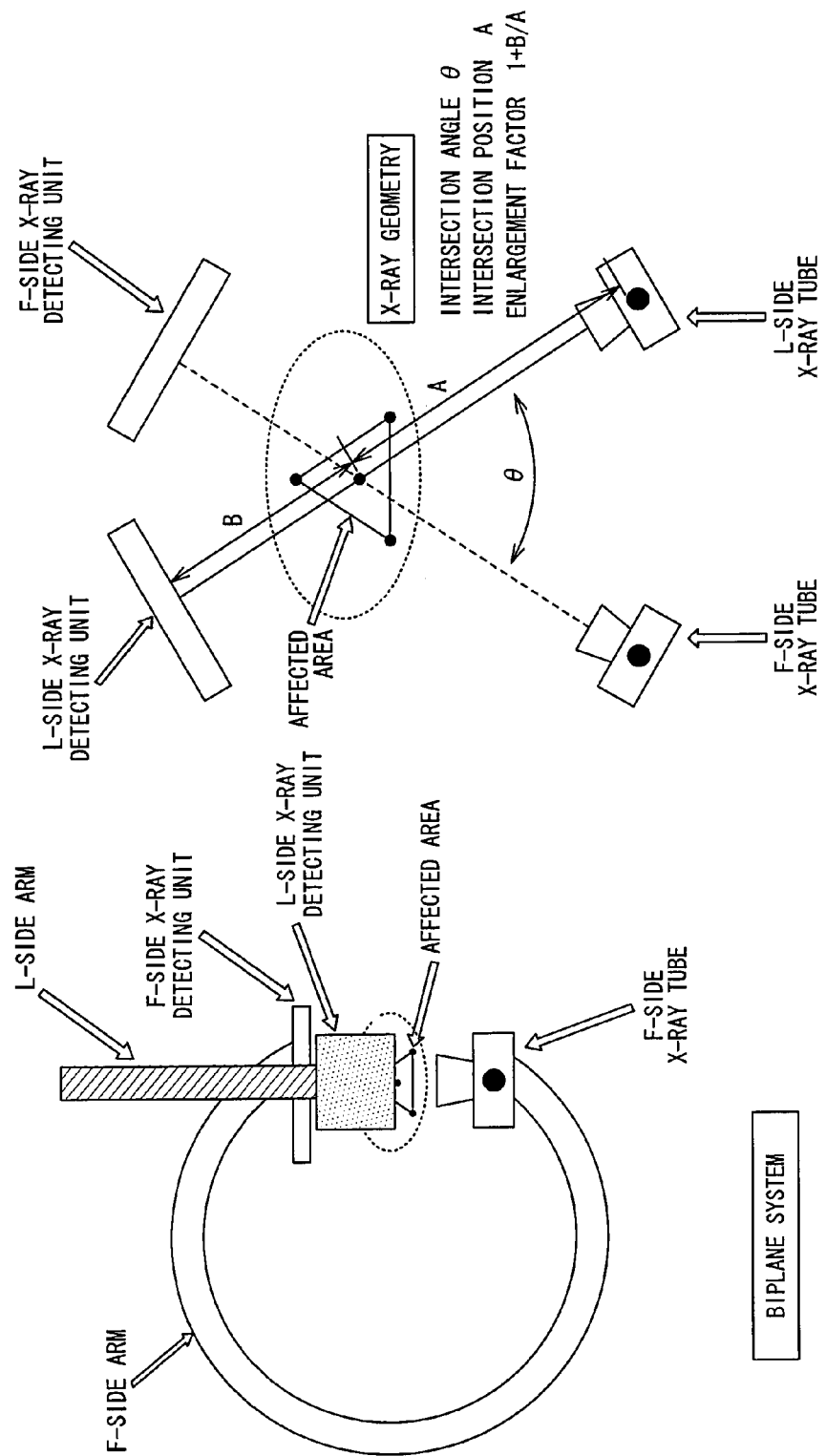
FIGS. 9(A) and 9(B) are views for describing an X-ray geometry of a biplane system.

FIG. 7 is a block diagram illustrating a configuration example of a medical image processing apparatus 1a according to a second embodiment. An imaging unit 10a according to the second embodiment is of a biplane system, and fluoroscopically images an affected area in two directions using X-rays. As illustrated in FIG. 9(A), the imaging unit 10a of the biplane system includes F-side (front-side) and L-side (lateral-side) arms, and the arms are respectively provided with an F-side X-ray tube and an F-side X-ray detecting unit and with an L-side X-ray tube and an L-side X-ray detecting unit. When the affected area is stereoscopically imaged by the imaging unit 10a of the biplane system, the F-side X-ray tube and the L-side X-ray tube are brought as close to each other as possible, whereby the intersection angle θ is set to be as small as possible.

Figure 8:
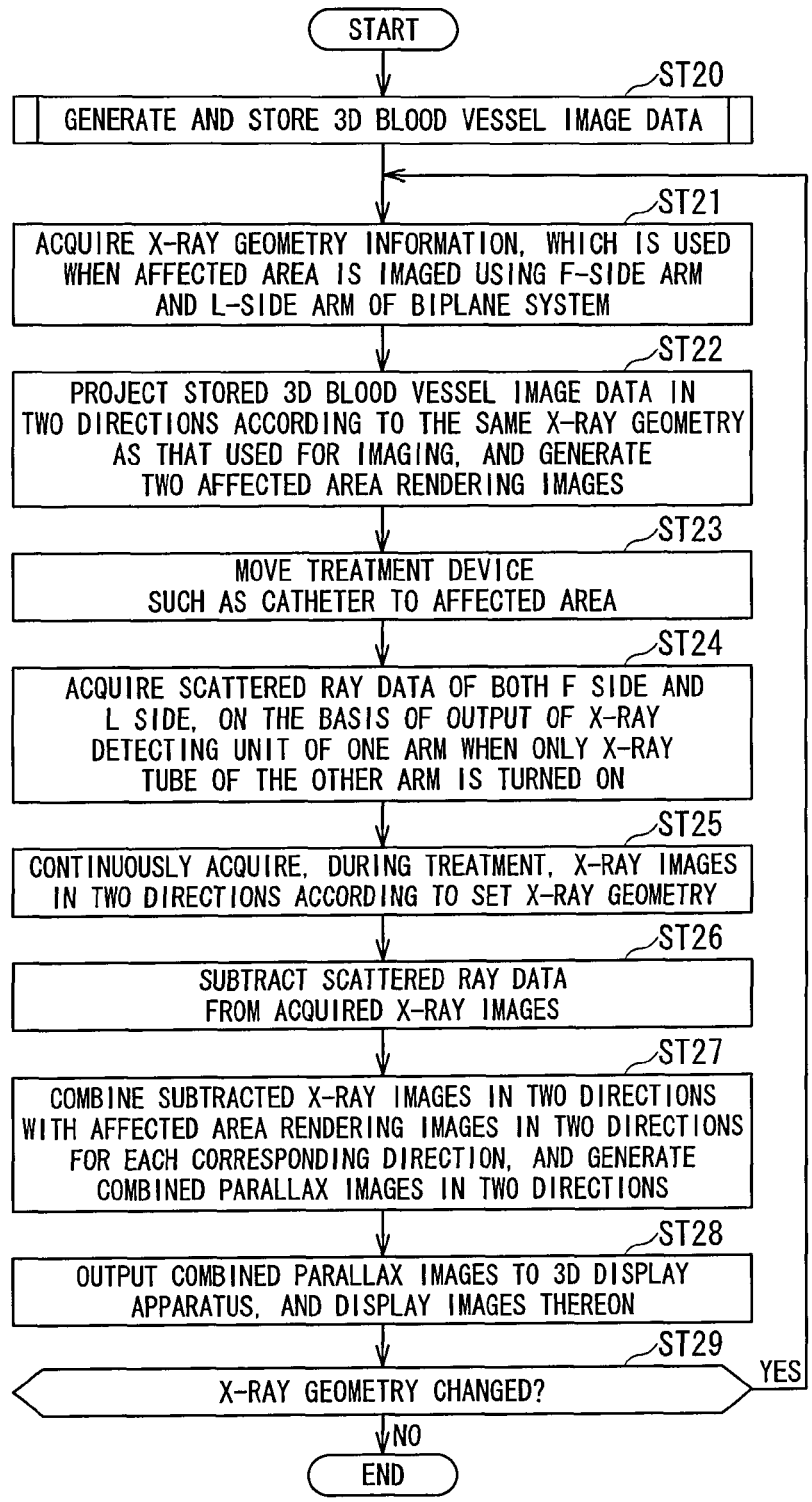
FIG. 8 is a flow chart illustrating an operation example of the medical image processing apparatus according to the second embodiment.

FIG. 8 is a flow chart illustrating an operation example of the medical image processing apparatus 1a according to the second embodiment. In Step ST20, one of the two X-ray tubes is moved around a patient, and three-dimensional blood vessel image data is generated and stored. A basic processing flow is the same as that in Steps ST10 to ST17 (FIG. 3) of the first embodiment, and the arm that is moved around the patient may be any one of the F-side arm and the L-side arm.

The processes in Steps ST21 to ST23 are similar to those of the first embodiment, and an X-ray geometry according to the second embodiment is determined depending on a positional relation between the F-side arm and the L-side arm as illustrated in FIGS. 9(A) and 9(B).

The processes in Step ST24 and Step ST26 are specific to the biplane system. The stereo X-ray tube system of the first embodiment has two right and left X-ray tubes and one X-ray detecting unit, and hence the right and left X-ray tubes are alternately turned on/off. That is, when one of the X-ray tubes is turned on, the other of the X-ray tubes is turned off. In contrast to this, in normal imaging of the biplane system of the second embodiment, the F-side and L-side X-ray tubes are turned on at the same time. Consequently, scattered rays from the F-side X-ray tube are detected by the L-side X-ray detecting unit, and scattered rays from the L-side X-ray tube are detected by the F-side X-ray detecting unit. The processes in Step ST24 and Step ST26 serve to eliminate an influence of such scattered rays.

In Step ST24, signals that are detected by the L-side X-ray detecting unit when only the F-side X-ray tube is turned on are averaged to obtain L-side scattered ray data. Next, signals that are detected by the F-side X-ray detecting unit when only the L-side X-ray tube is turned on are averaged to obtain F-side scattered ray data. This process is performed by an X-ray fluoroscopic image generating unit 20a, and the obtained L-side and F-side scattered ray data is stored as appropriate in a memory. The process in Step ST24 may be performed for a predetermined period, for example, a period of one frame immediately after the start of imaging.

Upon the end of the scattered ray data acquisition, in Step ST25, X-ray fluoroscopic imaging is started according to a set X-ray geometry and X-ray fluoroscopic images during the treatment are continuously acquired. In this fluoroscopic imaging, the F-side and L-side X-ray tubes are turned on at the same time, and hence the scattered rays have an influence thereon.

Accordingly, in Step ST26, the stored scattered ray data is subtracted from the acquired X-ray fluoroscopic images, and the influence of the scattered rays is removed.

The processes in Steps ST27 to ST29 are similar to those of the first embodiment. As illustrated in FIG. 6, the left and right X-ray fluoroscopic images (1) and (2) are combined with the affected area rendering images (1) and (2) for each corresponding direction, and an image of the affected area is stereoscopically displayed on the 3D display apparatus 100.

In the medical image processing apparatus 1a according to the second embodiment, similarly to the first embodiment, also in the case of fluoroscopic imaging of the biplane system, images are displayed on the 3D display apparatus 100 such that X-ray fluoroscopic images, which are taken in right and left parallax directions using the two F-side and L-side stereo X-ray tubes, are superimposed on rendering images, which are obtained by projecting three-dimensional blood vessel images of a head region according to the same X-ray geometry as that used for the X-ray fluoroscopic imaging. Accordingly, even in the case of a coiling treatment for an aneurysm or the like in a head region in which blood vessels run in a complicated manner, an operation of a catheter and the like can be easily and accurately performed.

(3) Third Embodiment

Figure 10:
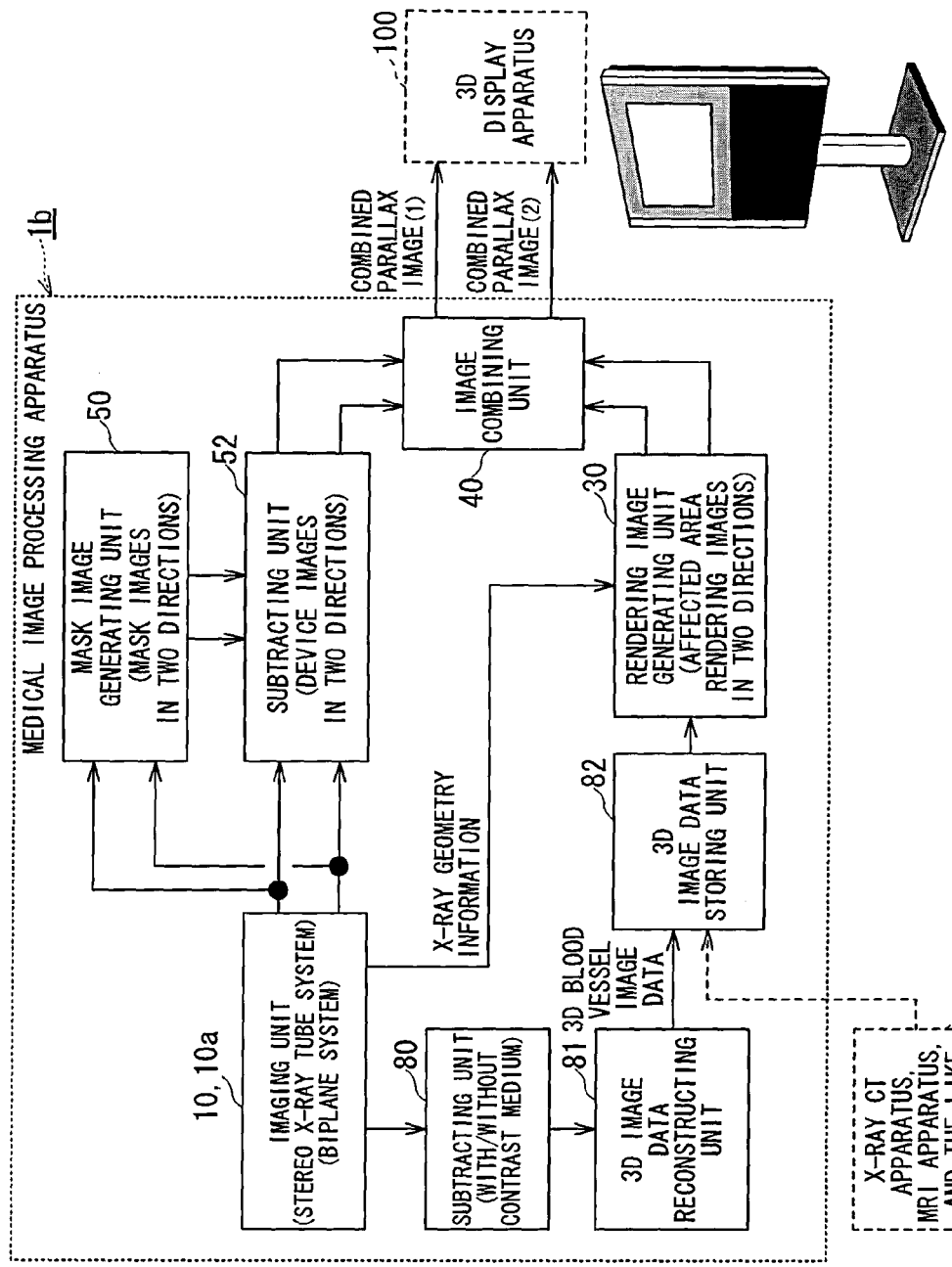
FIG. 10 is a block diagram illustrating a configuration example of a medical image processing apparatus according to a third embodiment.
Figure 11:
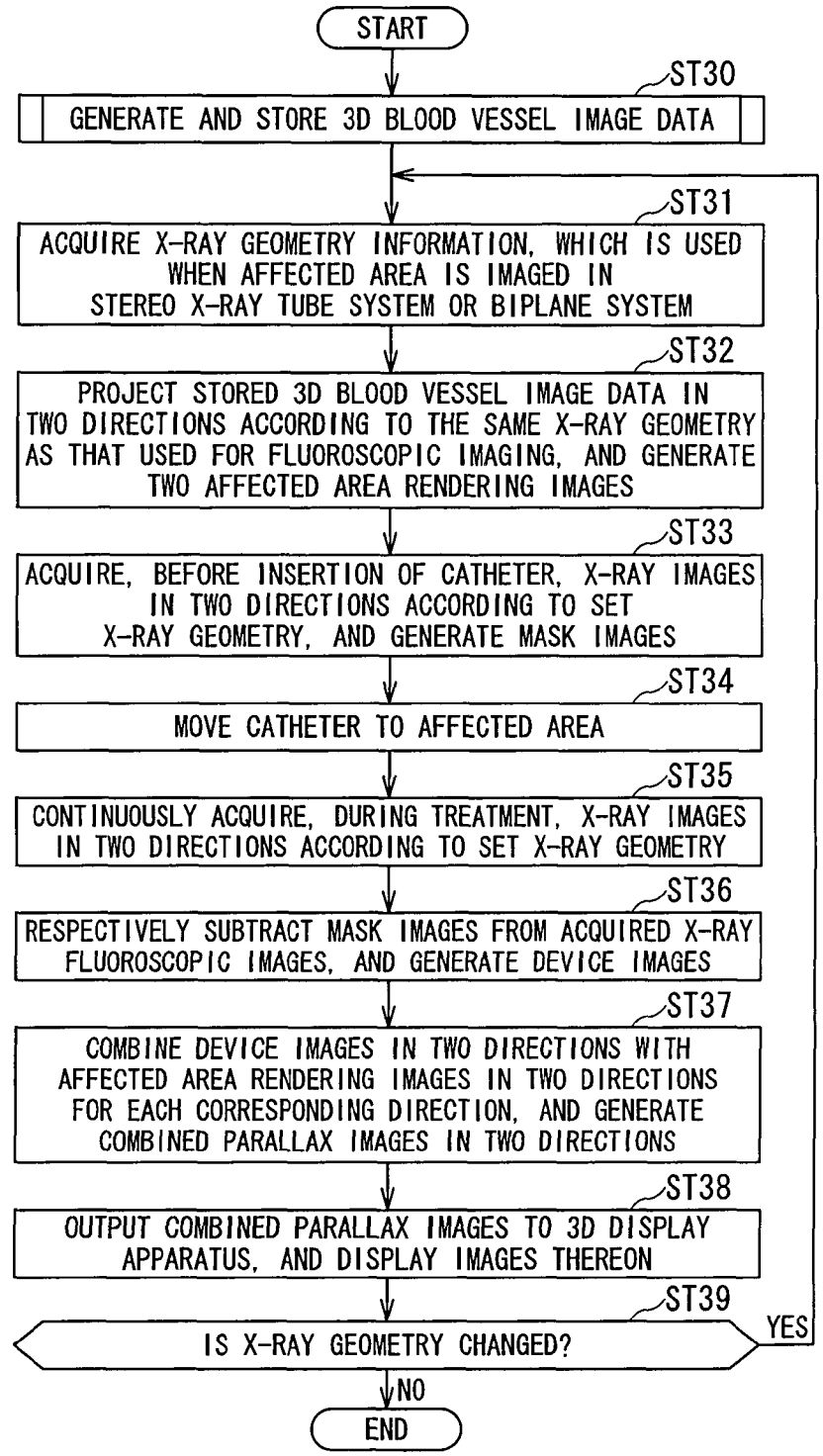
FIG. 11 is a flow chart illustrating an operation example of the medical image processing apparatus according to the third embodiment.

FIG. 10 is a block diagram illustrating a configuration example of a medical image processing apparatus 1b according to a third embodiment. The medical image processing apparatus 1b according to the third embodiment includes a mask image generating unit 50 and a subtracting unit 52 instead of the X-ray fluoroscopic image generating units 20 and 20a according to the first and second embodiments. FIG. 11 is a flow chart illustrating an operation example of the medical image processing apparatus 1b according to the third embodiment. Note that, in the third embodiment, a stereo X-ray tube system and a biplane system are substantially the same in processing, and hence description is given with reference to a common block diagram (FIG. 10) and a common flow chart (FIG. 11).

The processes in Steps ST30 to Step ST32 of FIG. 11 are the same as those of the first and second embodiments, and hence description thereof is omitted.

Figure 12:
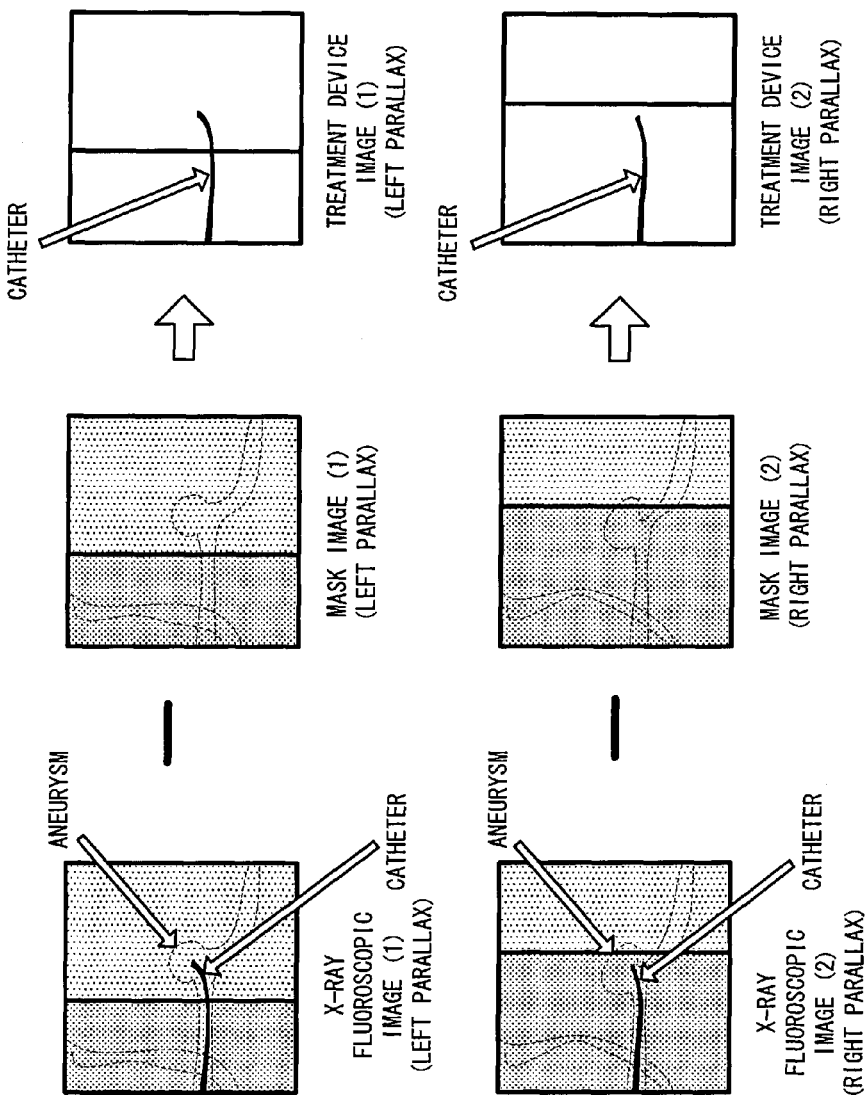
FIG. 12 is a view for describing a method of generating treatment device images on which only a treatment device is extracted using mask images.

In Step ST33, before a treatment device such as a catheter is inserted into a patient, X-ray fluoroscopic images are acquired in two directions according to a set X-ray geometry, and mask images are generated. The mask images are generated by, for example, averaging pixel values of a plurality of X-ray fluoroscopic images in the same direction. As illustrated in the center of FIG. 12, on the mask images, only a parenchymal portion around blood vessels and an affected area of an aneurysm are imaged, while the treatment device such as the catheter are not imaged. The blood vessels and the aneurysm also are not imaged since a contrast medium is not introduced. The mask images are generated by the mask image generating unit 50. The generated mask images (1) and (2) in left and right parallax directions are stored in an appropriate memory included in the mask image generating unit 50.

Upon the start of the treatment, the treatment device such as the catheter is moved toward the affected area (Step ST34). During this operation, X-ray fluoroscopic images are continuously acquired in the two directions according to the set X-ray geometry (Step ST35). As illustrated in the left of FIG. 12, on the X-ray fluoroscopic images acquired in this step, the treatment device such as the catheter is imaged in addition to the parenchymal portions around the blood vessels and the affected area of the aneurysm. Note that the blood vessels and the aneurysm are not imaged, since contrast medium is not introduced at this stage. In Step ST36, the previously stored mask images (1) and (2) are sequentially subtracted from the continuously acquired X-ray fluoroscopic images (1) and (2), respectively. The parenchymal portions around the blood vessels and the affected area of the aneurysm are removed by the subtraction from the acquired X-ray fluoroscopic images, and as illustrated in the right of FIG. 12, treatment device images (1) and (2) on which only the treatment device is extracted are generated. The process in Step ST36 is performed by the subtracting unit 52.

Figure 13:
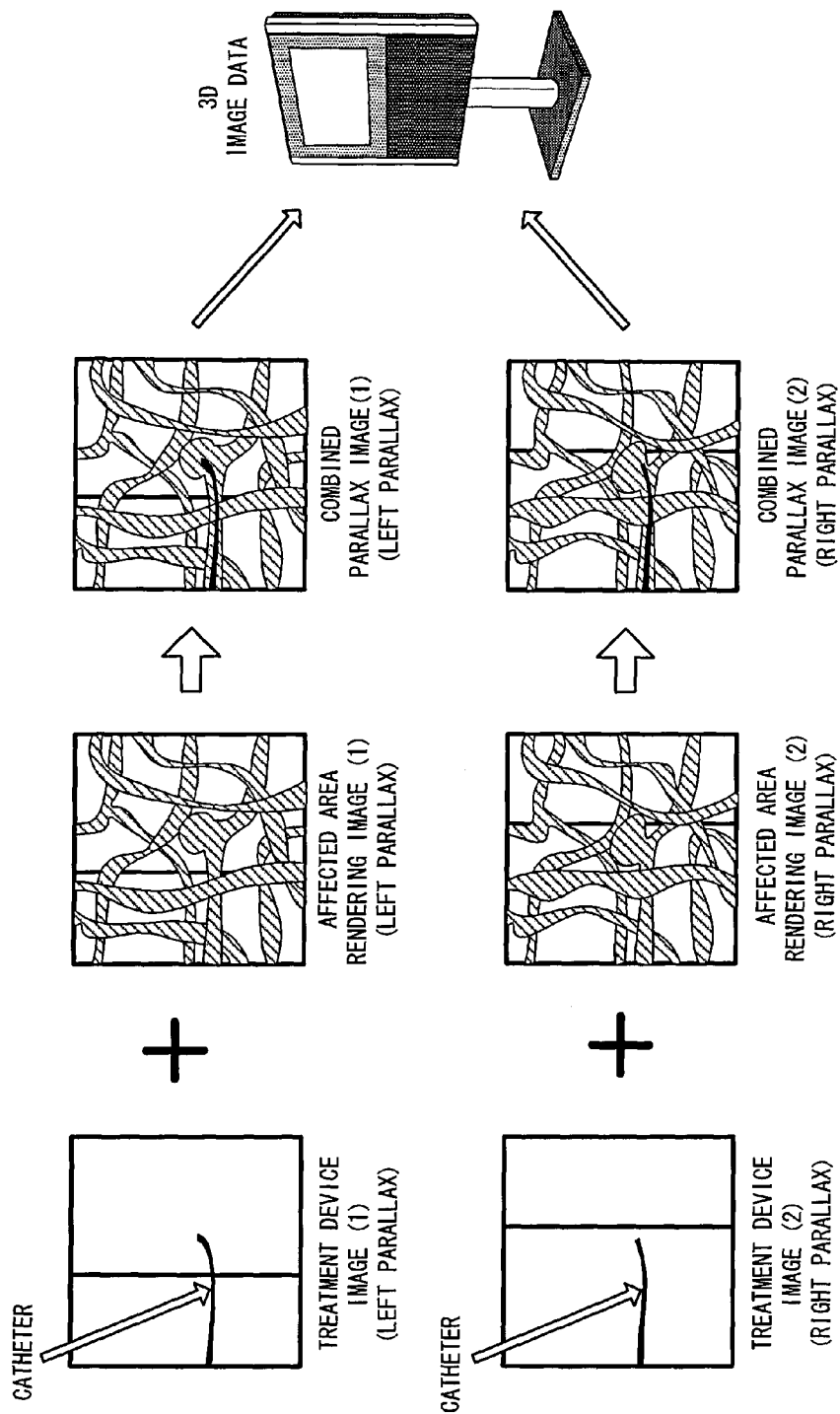
FIG. 13 is a view for describing a generation concept of combined parallax images according to the third embodiment.

In Step ST37, as illustrated in FIG. 13, the generated treatment device images (1) and (2) are respectively combined with the affected area rendering images (1) and (2) generated and stored in Step ST32. Then, the resultant combined parallax images are outputted to the 3D display apparatus 100 to be three-dimensionally displayed thereon (Step ST38). If the X-ray geometry is changed through an operation of a doctor or the like, the process returns to Step ST31 (Step ST39).

In the medical image processing apparatus 1b according to the third embodiment, images are displayed such that treatment device images, in which only a shape and movement of a treatment device such as a catheter are extracted, are combined with affected area rendering images. Accordingly, in addition to effects produced by the first and second embodiments, visual observation of the movement of the treatment device is facilitated, and device operability and treatment accuracy are improved. In addition, a positional relation between the treatment device and a blood vessel to be treated can be easily recognized by combining the treatment device images with the affected area rendering images, while such an advantage can not be obtained with only the treatment device images.

(4) Fourth Embodiment

Figure 14:
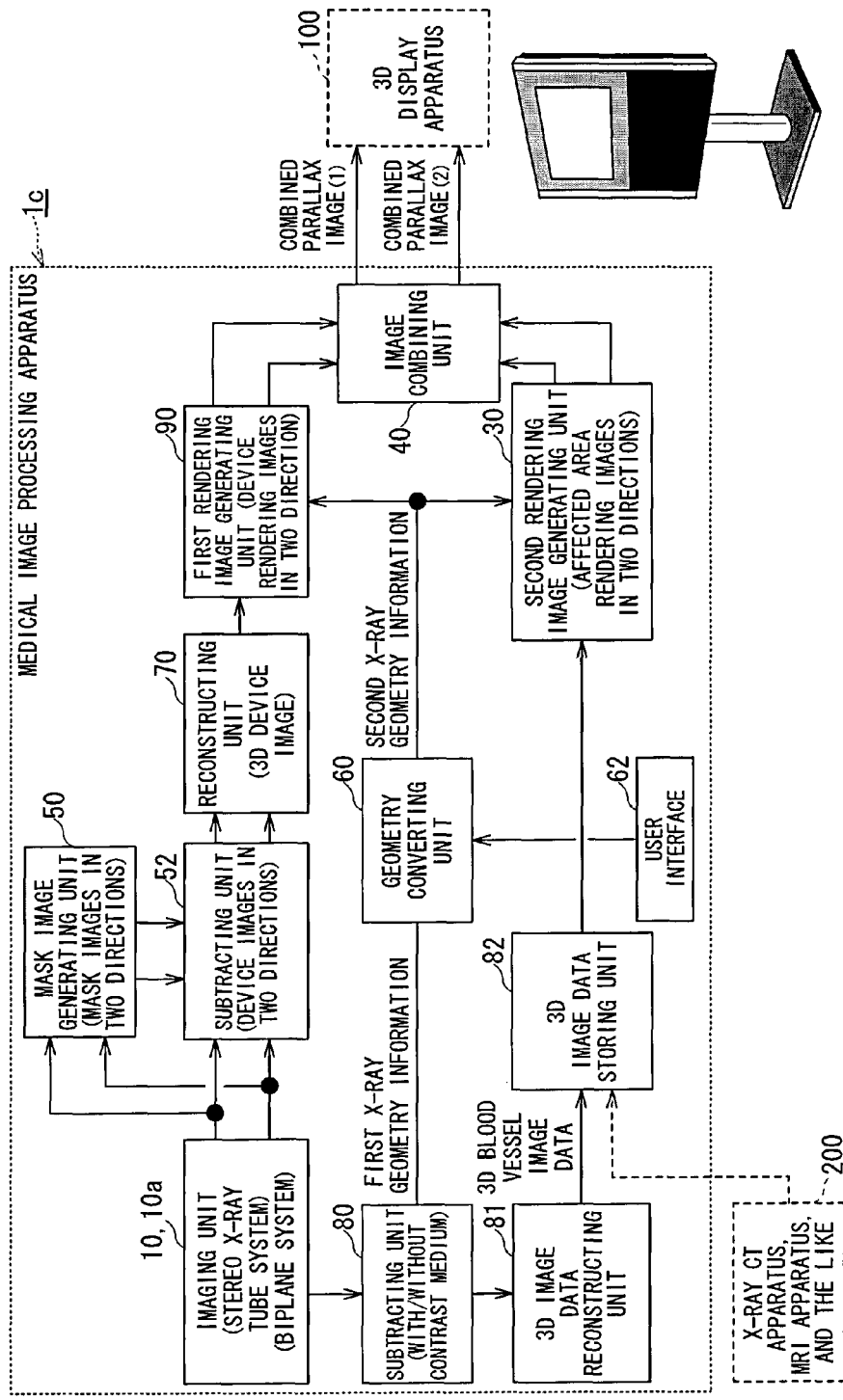
FIG. 14 is a block diagram illustrating a configuration example of a medical image processing apparatus according to a fourth embodiment.

FIG. 14 is a block diagram illustrating a configuration example of a medical image processing apparatus 1c according to a fourth embodiment. The medical image processing apparatus 1c according to the fourth embodiment includes a geometry converting unit 60, a user interface 62, a reconstructing unit 70, and a first rendering image generating unit 90, in addition to the configuration (FIG. 10) of the third embodiment. Note that a second rendering image generating unit 30 is practically the same as the rendering image generating unit 30 in FIG. 10.

In the fourth embodiment, a geometry (first X-ray geometry) used for X-ray fluoroscopic imaging is converted into a second X-ray geometry different therefrom, and then three-dimensional blood vessel image data is projected using the second X-ray geometry to generate affected area rendering images observed in two directions.

Meanwhile, the treatment device images in the two directions that are used for the 3D display in the third embodiment are once converted into three-dimensional image data (hereinafter, referred to as three-dimensional device image data). Then, the three-dimensional device image data is similarly projected using the second X-ray geometry to generate device rendering images.

After that, the device rendering images are combined with the affected area rendering images, both the images being projected (rendered) in the two directions according to the same second X-ray geometry. The resultant combined images are outputted to the 3D display apparatus 100.

Figure 15:
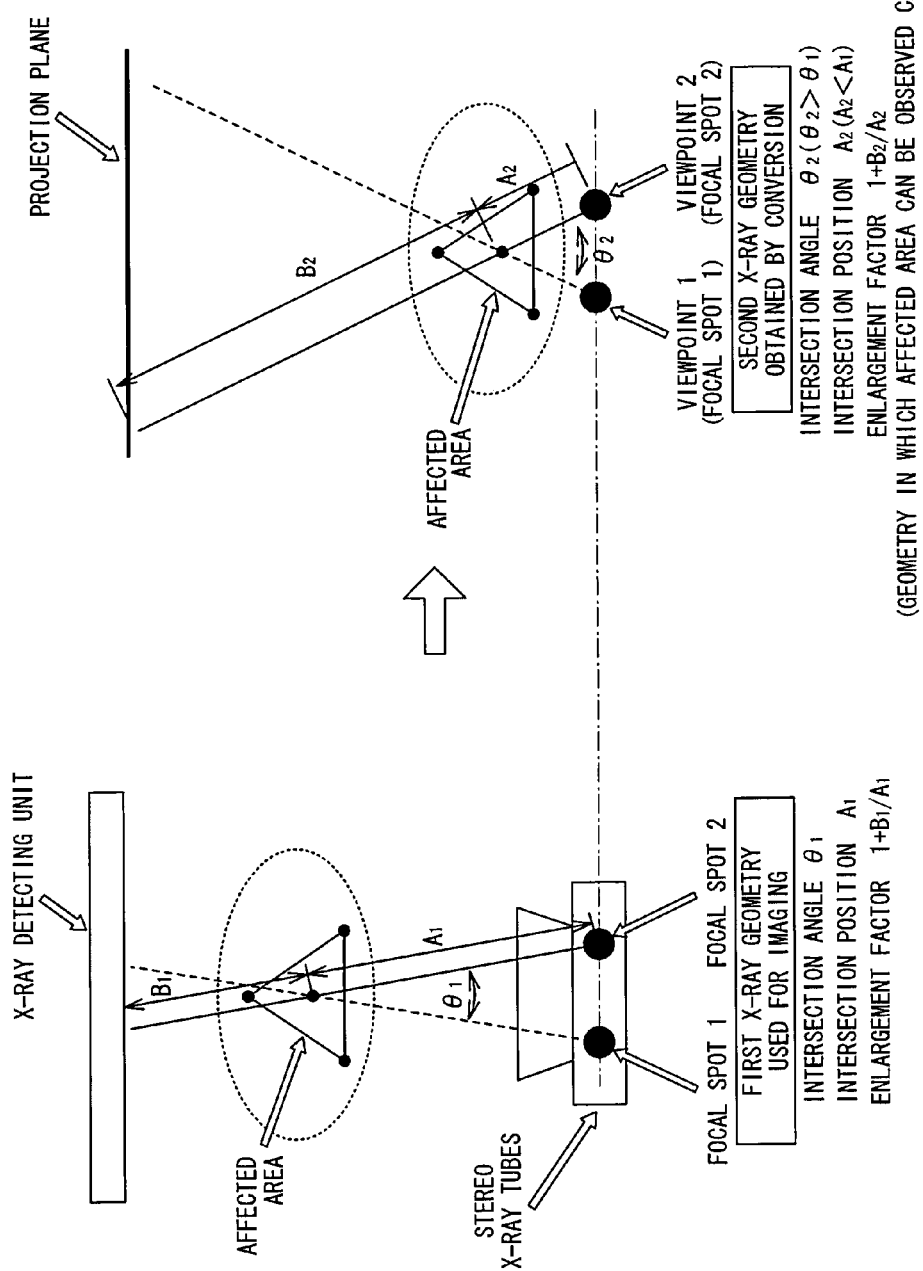
FIGS. 15(A) and 15(B) are views for describing a relation between a first X-ray geometry and a second X-ray geometry used for rendering according to the fourth embodiment.

FIGS. 15(A) and 15(B) are views schematically illustrating a relation between the first X-ray geometry (FIG. 15(A)) used for actual X-ray fluoroscopic imaging and the second X-ray geometry (FIG. 15(B)) used for a rendering process in the fourth embodiment. In the second X-ray geometry used in the fourth embodiment, as illustrated in FIG. 15(B), a distance $A_2$ (intersection position) between an affected area and viewpoints (corresponding to focal spots of X-ray tubes) is set to be smaller than a distance $A_1$ between the affected area and the focal spots of the X-ray tubes in the actual imaging. As a result, in the second X-ray geometry, the intersection angle $\theta_2$ between the two X-ray center trajectories is set to be larger than the intersection angle $\theta_1$ in the first X-ray geometry, and the enlargement factor $(1+B_2/A_2)$ is also set to be larger than the enlargement factor $(1+B_1/A_1)$ in the first X-ray geometry. According to the second X-ray geometry, the affected area can be brought closer and more enlarged for observation compared with the first X-ray geometry. With this configuration, in such a case where a leading end of a catheter is set in an aneurysm, a position of the leading end of the catheter in the depth direction can be recognized more easily.

Figure 16:
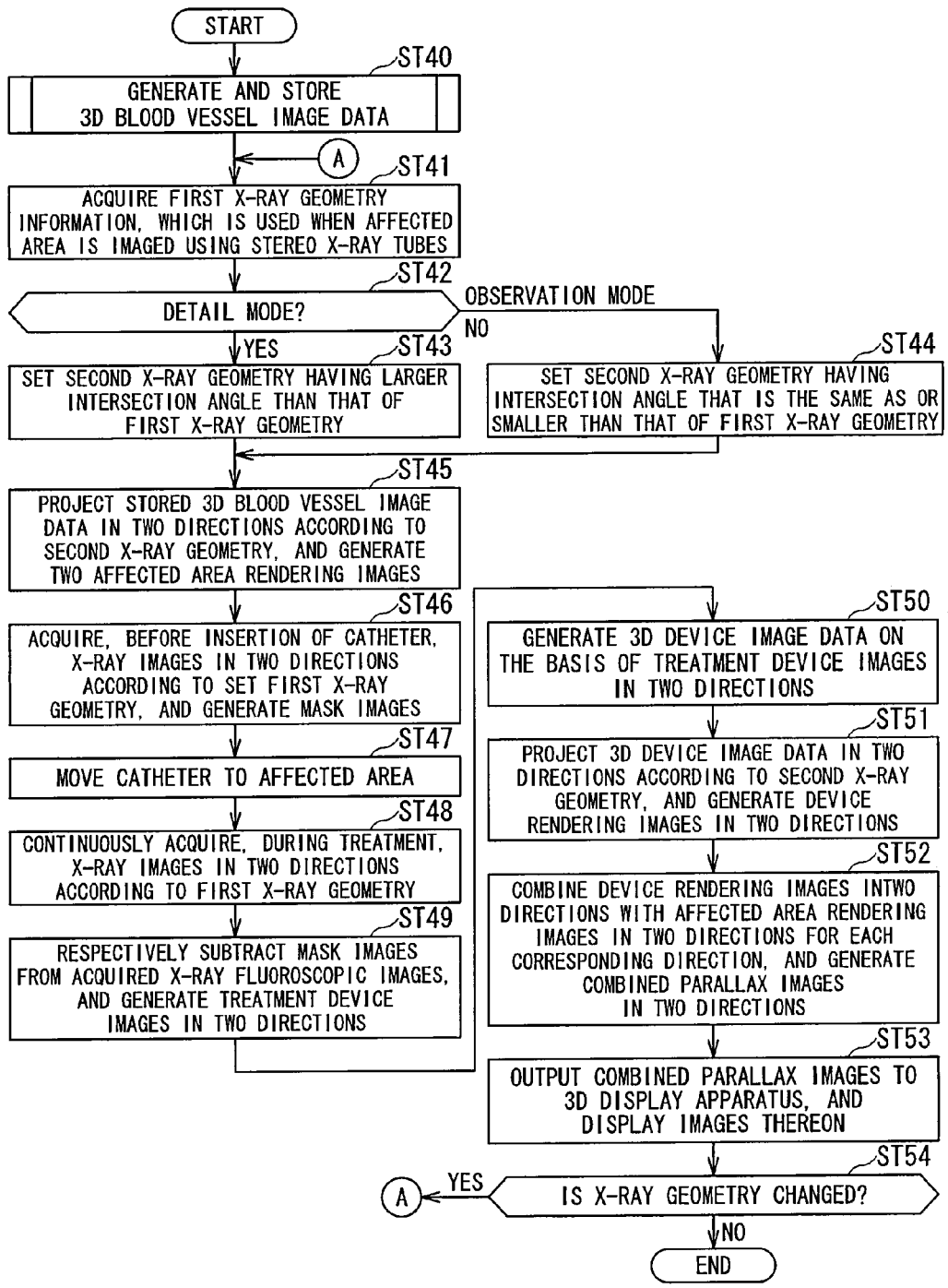
FIG. 16 is a flow chart illustrating an operation example of the medical image processing apparatus according to the fourth embodiment.

FIG. 16 is a flow chart illustrating an operation example of the medical image processing apparatus 1c according to the fourth embodiment. The processes in Step ST40 and Step ST41 are the same as those in Step ST30 and Step ST31 (FIG. 11).

In the fourth embodiment, a "detail mode" or an "observation mode" is set using the user interface 62 by a doctor or the like. The detail mode is set when the affected area is desired to be brought closer and more enlarged for observation than the normal "observation mode".

In Step ST42, it is determined which of the detail mode and the observation mode is set. If the detail mode is set, the second X-ray geometry having a larger intersection angle than that of the first X-ray geometry is set in Step ST43.

An image that is projected according to the second X-ray geometry is a highly precise image that enables closer observation of the affected area than normal. However, if an observer fixes his/her eyes on this image for a long time, the observer develops a feeling of exhaustion. Thus, in such a case, switching from the detail mode to the observation mode is possible. In the observation mode, the second X-ray geometry having an intersection angle that is the same as or smaller than that of the first X-ray geometry is set (Step ST44). The second X-ray geometry set in Step ST43 or Step ST44 is used in the processes in Step ST45 and the subsequent steps.

Note that, in the flow chart of FIG. 16, the switching between two modes, that is, the detail mode and the observation mode is given as an example for the second X-ray geometry, but the switching may be set more in detail or at multiple stages through the user interface 62.

Figure 18:
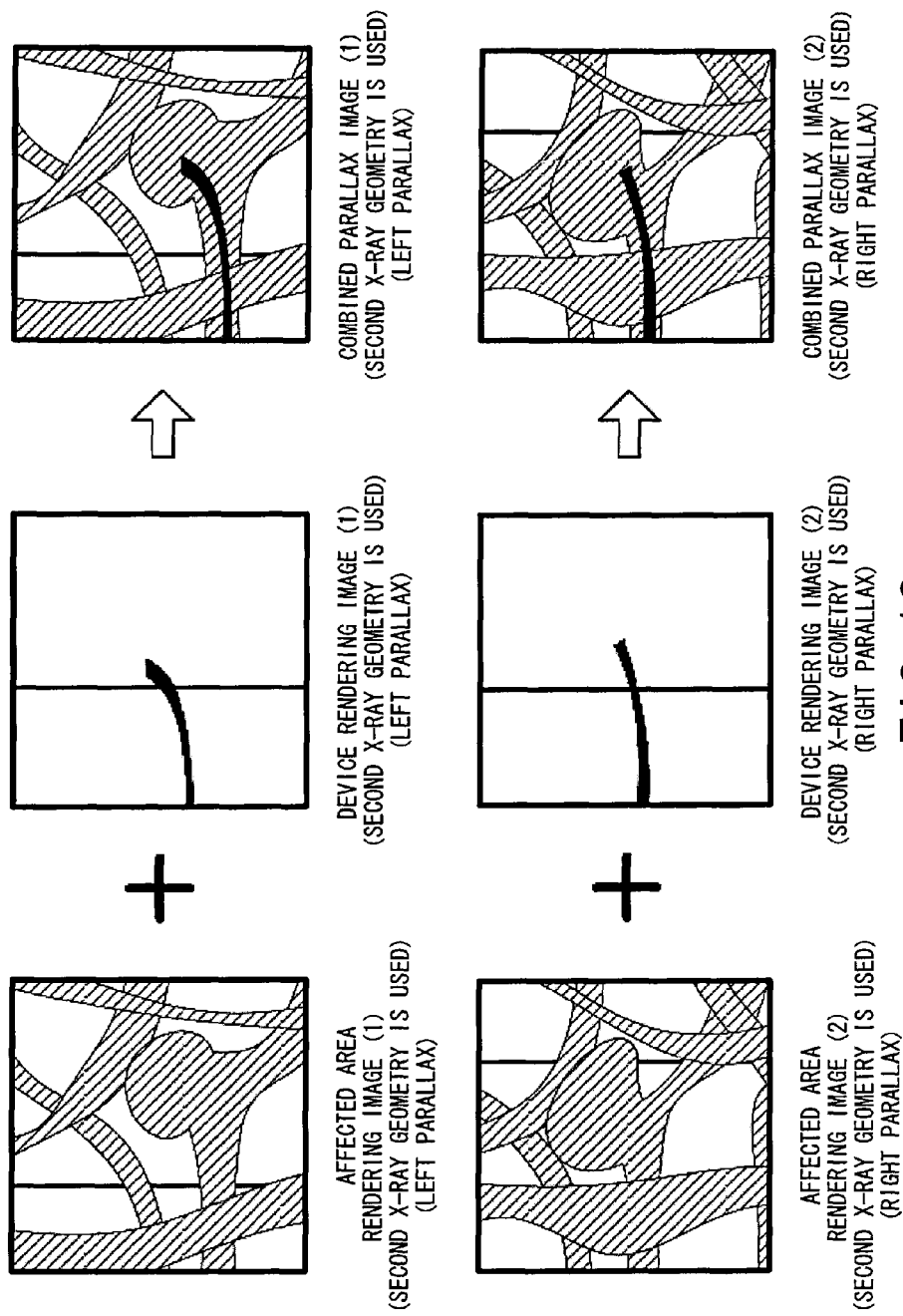
FIG. 18 is a view for describing a generation concept of combined parallax images according to the fourth embodiment.

In Step ST45, the stored three-dimensional blood vessel image data is projected in two directions according to the second X-ray geometry, and affected area rendering images observed in the two directions are generated. In the case where the detail mode is selected, affected area rendering images on which the affected area is enlarged are generated as illustrated in the left of FIG. 18.

The processes in Step ST46 to Step ST49 are the same as the processes in Step ST33 to Step ST36 (FIG. 11) of the third embodiment, and treatment device images on which only the treatment device is extracted using mask images are sequentially generated in the two directions.

Figure 17:
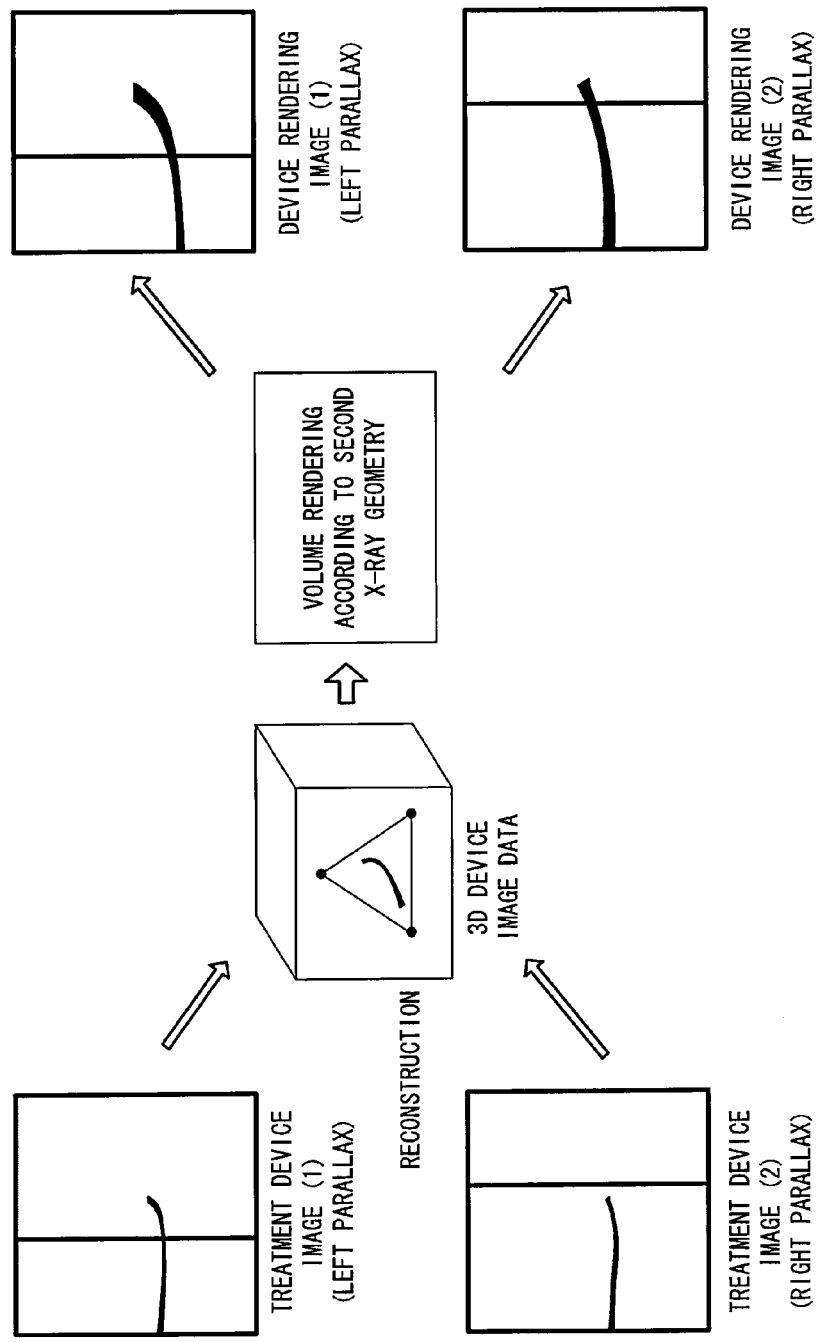
FIG. 17 is a view for describing a method of generating three-dimensional device image data using treatment device images in two directions and further generating device rendering images.

In Step ST50, three-dimensional device image data is reconstructed on the basis of the treatment device images (1) and (2) on which the treatment device is observed in the two directions. FIG. 17 schematically illustrates, in its center left, the reconstructed three-dimensional device image data.

The treatment device such as the catheter can be detected as linear components in two directions, from the treatment device images (1) and (2). It is possible to reconstruct a linear shape as three-dimensional data on the basis of the linear components in the two directions. An example method for such reconstruction involves geometrically reconstructing the three-dimensional data on the basis of a positional relation between the linear components in the two directions. Alternatively, an iterative approximate reconstruction method with priori information may be adopted therefor, and this method is described in a known document ("Reconstruction of blood vessels from an insufficient number of projections obtained from venography", Satoru Ohishi et al, Optical Communications 102 (1993) 425-431). Examples of the priori information include: three-dimensional continuity of signals based on the fact that continuous components are highly likely to be signals; and volume information based on the fact that components having a smaller volume are closer to the treatment device such as the catheter.

Note that an image of the entire treatment device does not necessarily need to be reconstructed, and only the leading end of the catheter may be reconstructed. In addition, instead of the leading end of the catheter, a marker attached to the leading end may be extracted, and the extracted marker may be reconstructed. The three-dimensional device image data is generated by the reconstructing unit 70.

In Step ST51, the three-dimensional device image data is projected (that is, subjected to volume rendering) in two directions according to the second X-ray geometry, and device rendering images (1) and (2) are generated in the two directions. In this step, if the detail mode is set, the device rendering images (1) and (2) are generated as illustrated in the right of FIG. 17 so as to be closer to the treatment device and more enlarged than the treatment device images obtained according to the first X-ray geometry.

In Step ST52, the device rendering images in the two directions are combined with the affected area rendering images for each corresponding direction, and combined parallax images are generated in the two directions. The generated combined parallax images are outputted to the 3D display apparatus 100 to be three-dimensionally displayed thereon.

FIG. 18 is a view illustrating a generation concept of the combined parallax images when the detail mode is set. According to the second X-ray geometry used in the detail mode, the affected area is brought closer to the viewpoints, and hence both the affected area rendering images and the device rendering images are enlarged. This enlargement is not simply made on a two-dimensional plane, but information on the depth direction of the affected area is reflected in this enlargement. Accordingly, the affected area can be observed closer than normal, and a highly precise treatment is possible.

(5) Fifth Embodiment

A fifth embodiment resembles the fourth embodiment, but is different therefrom in that: 1) the biplane system is used for the imaging unit instead of the stereo X-ray tube system; and 2) an intersection angle in the first X-ray geometry is set to be relatively large for X-ray fluoroscopic imaging, whereas an intersection angle in the second X-ray geometry is set to be smaller than that in the first X-ray geometry.

Figure 19:
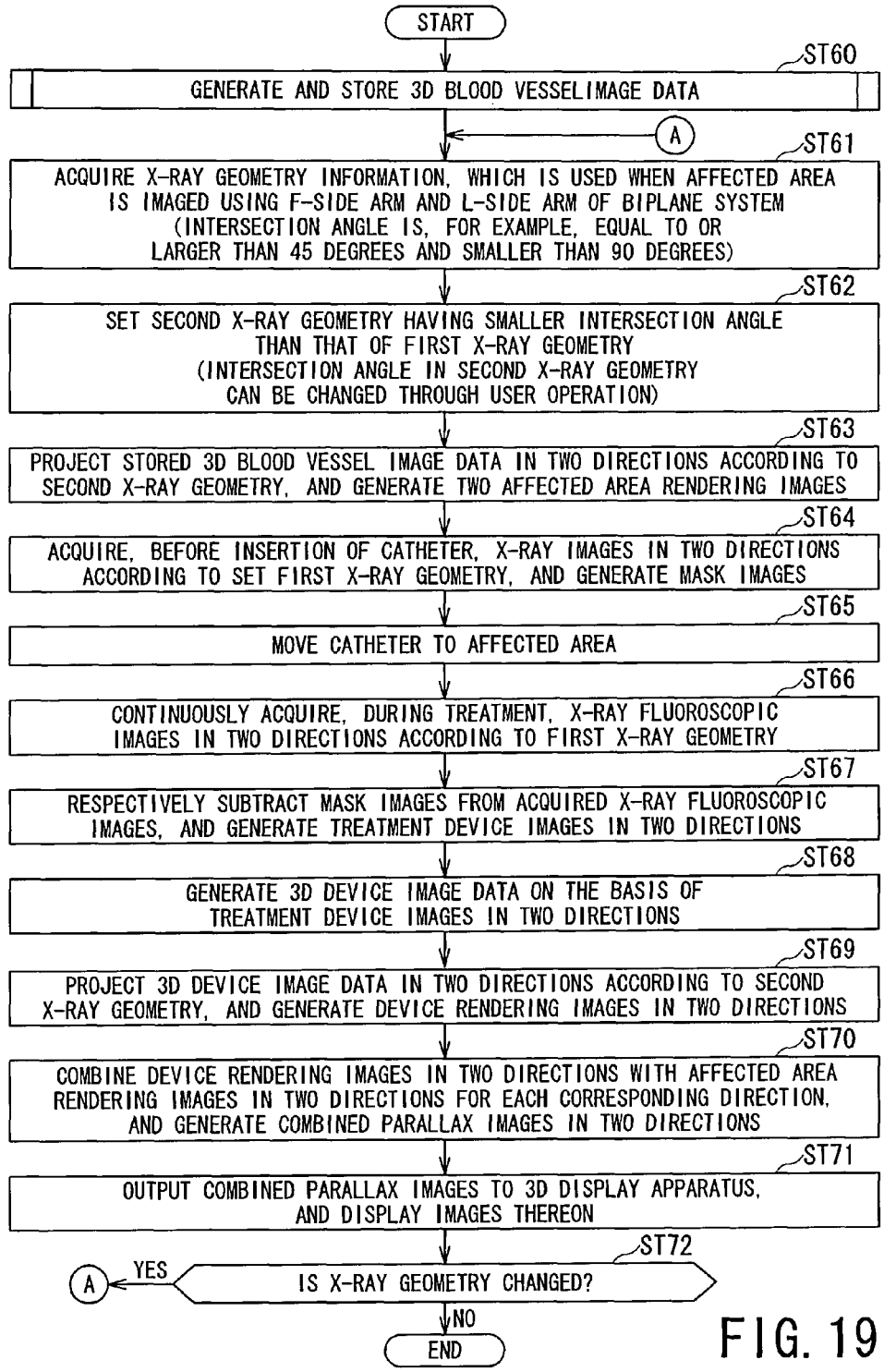
FIG. 19 is a flow chart illustrating an operation example of a medical image processing apparatus according to a fifth embodiment.

FIG. 19 is a flow chart illustrating an operation example according to the fifth embodiment. The flow chart of the fifth embodiment is different from that of the fourth embodiment in Step ST61 and Step ST62. Step ST60 is the same as Step ST40 in the fourth embodiment, and Step ST63 to Step ST72 are the same as Step ST45 to Step ST54 in the fourth embodiment. Hence, description thereof is omitted.

In Step ST61, first X-ray geometry information, which is used for X-ray fluoroscopic photographing of an affected area using the F-side and L-side arms of the biplane system, is acquired. Here, an intersection angle $\theta_1$ between the X-ray center trajectories in the first X-ray geometry is set to a relatively large value, for example, a range that is equal to or larger than 45 degrees and smaller than 90 degrees (see FIG. 20(A)).

In Step ST62, the second X-ray geometry having a smaller intersection angle than that of the first X-ray geometry is set.

In the fifth embodiment, the affected area is fluoroscopically imaged using X-rays according to the first X-ray geometry having a large intersection angle, and hence angle information on the affected area at the time of the imaging can be acquired with high precision. Unfortunately, if this large intersection angle is used as a parallax angle for projection and the rendering images are generated to be three-dimensionally displayed, a large burden is placed on an observer to easily exhaust him/her. Accordingly, the device rendering images and the affected area rendering images are generated according to the second X-ray geometry in which the intersection angle is set to be smaller than that used for the imaging, and combined parallax images obtained by combining these images are outputted to the 3D display apparatus 100. As a result, images having high-precision angle information can be three-dimensionally displayed for the observer with no burden being placed on him/her.

As has been described hereinabove, the medical image processing apparatus according to each of the embodiments enables an operator to easily understand a front-back and right-left positional relation of blood vessels in and around an affected area of an aneurysm or the like, and can provide a stereoscopic image that contributes to an accurate catheter operation without any error, even in an area in which the blood vessels run in a complicated and intricate manner.

Some embodiments of the present invention have been presented above merely as examples, and thus do not limit the scope of the present invention. These embodiments can be carried out in other various modes, and can be variously omitted, replaced, and modified in a range not departing from the gist of the present invention. These embodiments and modifications thereof are included in the scope and gist of the present invention, and are also included in the invention described in WHAT IS CLAIMED IS and a range equivalent thereto.

What is claimed is:

1. A medical image processing apparatus, comprising:
   an imaging unit configured to image an affected area in two directions using X-rays;
   a mask image generating unit configured to image the affected area before a device for treating the affected area is brought closer to the affected area, to thereby generate first and second mask images corresponding to the two directions;
   a subtraction processing unit configured
      to image the affected area while bringing the device closer to the affected area, to thereby generate first and second X-ray fluoroscopic images corresponding to the two directions, and
      to subtract the first and second mask images from the generated first and second X-ray fluoroscopic images, to thereby generate first and second treatment device images on which movement of the device is extracted;
   a reconstructing unit configured to reconstruct images of the device as three-dimensional data on a basis of the first and second treatment device images, to thereby generate three-dimensional device image data;
   a first rendering image generating unit configured to project the three-dimensional device image data in two directions according to a second X-ray geometry that is different from a first X-ray geometry used for imaging the first and second X-ray fluoroscopic images, to thereby generate first and second device rendering images;
   a second rendering image generating unit configured to project the affected area contained in three-dimensional image data acquired in advance, in two directions according to the second X-ray geometry, to thereby generate first and second affected area rendering images; and
   an image combining unit configured to combine the first and second device rendering images with the first and second affected area rendering images for each corresponding direction, to thereby generate combined parallax images in two parallax directions corresponding to the two directions, and to output the two generated combined parallax images.

2. The medical image processing apparatus according to claim 1, wherein
   the first and second X-ray geometries each are a geometric positional relation including an intersection angle between X-ray center trajectories in the two directions, and
   the intersection angle in the second X-ray geometry is larger than the intersection angle in the first X-ray geometry.

3. The medical image processing apparatus according to claim 2, wherein the imaging unit includes first and second X-ray focal spots, and is configured as a stereo X-ray tube system in which emitted X-rays are detected by one X-ray detecting unit while the first and second X-ray focal spots are switched therebetween.

4. The medical image processing apparatus according to claim 1, wherein
   the first and second X-ray geometries each are a geometric positional relation including an intersection angle between X-ray center trajectories in the two directions, and
   the intersection angle in the first X-ray geometry is larger than the intersection angle in the second X-ray geometry.

5. The medical image processing apparatus according to claim 4, wherein the imaging unit includes first and second arms that are independently rotatable, and is configured as a biplane system in which: the first arm is provided with a first X-ray tube and a first X-ray detecting unit; and the second arm is provided with a second X-ray tube and a second X-ray detecting unit, and
   the first and second mask images and the first and second X-ray fluoroscopic images are imaged with the first and second X-ray tubes being turned on at the same time.

6. The medical image processing apparatus according to claim 1, wherein
   the first and second X-ray geometries each are a geometric positional relation including an intersection angle between X-ray center trajectories in the two directions, either a detail mode or an observation mode is selected through a user operation, and when the detail mode is selected, the intersection angle in the second X-ray geometry is set larger than that in the observation mode.

\* \* \* \* \*